(12) United States Patent
 Trygstad et al.

(10) Patent No.: US 8,849,582 B2
(45) Date of Patent: Sep. 30, 2014

(54) OFFLINE ANALYZER SYSTEM AND METHOD FOR MULTIVARIATE CHARACTERIZATION OF PROPERTIES IN CRUDE AND HEAVY HYDROCARBON OILS

(75) Inventors: W. Marcus Trygstad, Spring, TX (US); Bruce Keen, Bartlesville, OK (US); Russell Jackson, Sudbury, MA (US)

(73) Assignee: Invensys Systems, Inc., Foxboro, MA (US)

( * ) Notice: Subject to any disclaimer, the term of this patent is extended or adjusted under 35 U.S.C. 154(b) by 478 days.

(21) Appl. No.: 13/329,597

(22) Filed: Dec. 19, 2011

(65) Prior Publication Data

US 2012/0158315 A1 Jun. 21, 2012

Related U.S. Application Data

(60) Provisional application No. 61/425,488, filed on Dec. 21, 2010, provisional application No. 61/431,307, filed on Jan. 10, 2011.

(51) Int. Cl.
*G06F 19/00* (2011.01)
*G01N 21/85* (2006.01)
*G01N 21/35* (2014.01)
*G01N 33/28* (2006.01)
*G01N 21/03* (2006.01)
*G01N 21/05* (2006.01)

(52) U.S. Cl.
CPC ............ *G01N 21/85* (2013.01); *G01N 21/0303* (2013.01); *G01N 21/05* (2013.01); *G01N 21/359* (2013.01); *G01N 33/2823* (2013.01); *G01N 21/3577* (2013.01)
USPC ......... 702/25; 702/11; 73/152.05; 73/152.28; 73/152.55; 166/264; 166/250.01

(58) Field of Classification Search
CPC .......... G01N 21/3577; G01N 33/2823; G01N 21/0303; G01N 21/85; G01N 21/359; G01N 21/05
USPC ....................... 702/11, 12, 22, 23, 25, 27, 30; 73/152.07, 152.05, 152.09, 152.11, 73/152.23, 152.24, 152.28, 152.55; 166/264, 250.01
See application file for complete search history.

(56) References Cited

U.S. PATENT DOCUMENTS

| | | | |
|---|---|---|---|
| 6,070,128 A * | 5/2000 | Descales et al. | 702/30 |
| 6,477,516 B1 * | 11/2002 | Colaiocco et al. | 706/21 |
| 6,991,045 B2 * | 1/2006 | Vinegar et al. | 175/45 |
| 7,055,600 B2 * | 6/2006 | Messier et al. | 166/250.01 |
| 7,063,145 B2 * | 6/2006 | Veenstra et al. | 166/250.01 |
| 7,066,254 B2 * | 6/2006 | Vinegar et al. | 166/245 |

(Continued)

*Primary Examiner* — Carol S Tsai
(74) *Attorney, Agent, or Firm* — Edward S. Jarmolowicz, Esq.

(57) ABSTRACT

A method and apparatus is provided for off-line concentration determination of components liquid hydrocarbon mixtures such as crude or heavy oil. A sampling unit continuously delivers a sample volume to a fluid flow path while a temperature control module maintains the sample at a predetermined setpoint temperature. A homogenization module helps prevent sample stratification while a flow control module maintain a constant sample flow rate. A spectrometer is communicably coupled to an optical transmission cell to transmit and receive radiation. The transmission cell includes collection optics to capture and aggregate non-collimated radiation emerging from the cell, for transmission to the spectrometer. The spectrometer measures sample spectra at a predetermined rate of flow of the sample volume through the transmission cell. A processor is configured to capture and use the spectra in combination with a model of spectra for the hydrocarbon mixture.

41 Claims, 15 Drawing Sheets

Scheme for property prediction through application of a property model

(56) References Cited

U.S. PATENT DOCUMENTS

| | | | |
|---|---|---|---|
| 7,066,257 B2 * | 6/2006 | Wellington et al. | 166/272.2 |
| 7,077,198 B2 * | 7/2006 | Vinegar et al. | 166/245 |
| 7,086,465 B2 * | 8/2006 | Wellington et al. | 166/272.1 |
| 7,356,410 B2 * | 4/2008 | Rode et al. | 702/2 |
| 7,379,819 B2 * | 5/2008 | Betancourt et al. | 702/11 |
| 7,461,691 B2 * | 12/2008 | Vinegar et al. | 166/60 |
| 7,587,290 B2 * | 9/2009 | Scott | 702/100 |
| 7,637,151 B2 * | 12/2009 | Raghuraman et al. | 73/152.55 |
| 8,109,334 B2 * | 2/2012 | Goodwin | 166/264 |
| 8,372,169 B2 * | 2/2013 | Tsangaris et al. | 48/120 |
| 2003/0205378 A1 * | 11/2003 | Wellington et al. | 166/302 |
| 2003/0209066 A1 * | 11/2003 | Goodwin | 73/152.05 |
| 2005/0288862 A1 * | 12/2005 | Rode et al. | 702/2 |
| 2007/0143023 A1 * | 6/2007 | Betancourt et al. | 702/11 |
| 2007/0209799 A1 * | 9/2007 | Vinegar et al. | 166/302 |
| 2008/0015792 A1 * | 1/2008 | Scott | 702/25 |
| 2008/0141767 A1 * | 6/2008 | Raghuraman et al. | 73/152.55 |
| 2008/0209807 A1 * | 9/2008 | Tsangaris et al. | 48/89 |
| 2008/0217261 A1 * | 9/2008 | Kapila et al. | 210/760 |
| 2011/0005745 A1 * | 1/2011 | Goodwin | 166/250.01 |
| 2011/0180262 A1 * | 7/2011 | O'Dowd | 166/303 |
| 2012/0232172 A1 * | 9/2012 | Tasaka et al. | 518/700 |

* cited by examiner

OFFLINE ANALYZER SYSTEM AND METHOD FOR MULTIVARIATE CHARACTERIZATION OF PROPERTIES IN CRUDE AND HEAVY HYDROCARBON OILS

RELATED APPLICATION

This application claims the benefit of U.S. Provisional Patent Application Ser. No. 61/425,488, entitled System and Method for Online, At Line and Off Line Crude and Heavy Oil Analysis, filed on Dec. 21, 2010, and U.S. Provisional Patent Application Ser. No. 61/431,307, entitled System and Method for Online, At Line and Off Line Crude and Heavy Oil Analysis, filed on Jan. 10, 2011, the contents both of which are incorporated herein by reference in their entireties for all purposes.

BACKGROUND

1. Technical Field

This invention concerns an apparatus and method for representative sampling, thermal conditioning, and analysis of laboratory quantities of non-homogeneous petroleum hydrocarbon samples such as crude oil and heavy oils.

2. Background Information

Physical and chemical properties of hydrocarbon streams in petroleum refining and petrochemical processes can be measured by a variety of technologies and methods. Such measurements represent information that can be used to by engineers to maintain throughput near the design limits of an operating unit, achieve property target values, maximize yields for a given feed, and minimize energy costs. However, attainment of process control and optimization objectives may be constrained when process samples are captured manually and submitted for laboratory analysis: results correspond to the point in time when the sample was captured; some properties or component concentrations may change before laboratory analysis if special care is not exercised during sampling or transport; and the frequency of manual sampling and analysis may be insufficient to detect important process changes. This fact has motivated the repackaging and automation of many laboratory methods to permit their implementation for online measurement. Most common are univariate analyzers in which the sensor element responds directly to the property or component of interest; water and sulfur content, viscosity, and density, are examples. With such sensors, a mathematical formula as simple as a linear equation calculates the property value of interest from the sensor's associated response, which, mathematically speaking, is a discrete function e.g. voltage, frequency, absorbance, conductivity, or simply intensity. Calibration is generally simple and can be performed easily online.

Though discrete analyzers are relatively inexpensive, convenient to install, and simple to operate, the very selectivity that makes them useful also tends to limit the extent to which they can enable rigorous optimization of processes that process and transform complex chemical mixtures. The issue is one of information content, or more precisely, the degrees of freedom in the mixture. Thus, hydrocarbon streams such as motor fuels, the components blended to produce them, and crude oil that is refined to produce the blending components are themselves complex mixtures that do not lend to full characterization with simple, discrete analyzers. Gasoline, for example, may contain hundreds of components while the number of components in crude oil typically exceeds 10,000. Accordingly, refinery process optimization may depend on measuring a property that itself derives from multiple parameters or components. A common example of this is the octane value of gasoline. Though traditionally measured with a knock engine as a simple, discrete property, octane is a function of the interplay between many variables including the proportions of aromatic, olefinic, paraffinic and isoparaffin compounds and molecular weight distribution. Another type of multivariate property is one that is not a single value, but an ensemble of related values. For example, the performance of gasoline and diesel as motor fuels depends on the temperatures at which certain percentages of the components distill from the mixture, hence the importance of the so-called T10, T50, and T90 values, i.e. the temperatures at which 10%, 50%, and 90% of the mixture distills under defined experimental conditions.

Given the central importance of distillation properties in regard to petroleum products, it follows that this is also the case for materials from which they are produced. Indeed, the true boiling point (TBP) distillation curve for crude oil feed affects the economics of the oil refining process through its direct impact on total throughput, the mix of products that can be produced, and energy consumed by the process. Sometimes referred to as the distillation curve or profile, each particular type of crude oil has an associated TBP curve, which is a plot relating distillation temperature and the percentage of material in the crude oil that has been distilled. A representative distillation curve for a hydrocarbon mixture is shown in FIG. 1.

Unfortunately, conventional methods for generating TBP distillation curves from crude oil samples involve the actual distillation of the sample in the laboratory using carefully calibrated apparatus that lends to a very limited level of automation and generally must be carried out by skilled technicians. Requiring 3-5 liters of sample and up to several days' time, this approach does not support rapid decision-making required when receiving crude oil from a ship or pipeline, or when feeding crude oil to the crude distillation unit (CDU) in the refinery, the first of many steps in the oil refining process. Refiners therefore have made attempts to ply analytical technologies like near infrared (NIR) spectroscopy in the hope of realizing benefits similar to those afforded by its application for multivariate analysis of hydrocarbon streams such as in gasoline and diesel, which are homogeneous, clear, and chemically simpler than crude oil.

NIR spectrometers belong to a class of advanced analyzers whose base response can be described in mathematical parlance as being a continuous function, a vector, an array, or a matrix. Rather than being one or several independent data points, the output of such analyzers comprises dozens or hundreds of points that define a continuous, complex function whose features are determined by the physical characteristics and chemical composition of the sample. Other examples of advanced analyzer technologies include NMR, FTIR, and Raman spectrometers. In some cases chromatographic data and outputs obtained through sample stimulation by microwave or ultrasonic signals also may have the form of a multivariable response matrix. The terms applied to such outputs describe the technology of origin, e.g. spectrometers and chromatographs yield spectra and chromatograms, respectively, which are x-y plots relating dependent responses measured across a continuum of independent values such as time, frequency, or wavelength. The general term response matrix will be used hereinafter when referring to outputs obtained from advanced analyzers generally, while spectrum may be used alternatively for those obtained from a spectrometer.

Generally, the components or properties of complex hydrocarbon mixtures being analyzed do not express themselves explicitly in sample spectra. For example, in the application of NIR spectroscopy to measure motor fuel properties, no single feature accounts exclusively for octane value, cetane index, or the temperatures for distillation yields mentioned previously. Rather, such properties are determined by the relative quantities of hundreds or thousands of compounds in the mixture, which express themselves across a relatively broad spectral range. Accordingly, multivariable property models must be developed which yield the property value of interest when applied to the entire response matrix of an unknown sample or to significant portions thereof. The terms property and component may be used interchangeably or in combination hereinafter to denote any of the following: the characteristics of the aggregate mixture, e.g. its density, response matrix, or spectrum; subsets of compounds in a mixture which share common physical characteristics, e.g. boiling point range; compounds sharing chemical functionality, e.g. paraffins, naphthenes, aromatics, and asphaltenes; and individual compounds, e.g. toluene and hexadecane. Generally, a component is understood to be an isolable compound or group of compounds that share common chemical functionality or physical properties; whereas a property is understood to be a physical attribute of either the hydrocarbon mixture as a whole or of a component.

While these advanced analyzers/spectrometers have been used with broad success to measure properties of relatively light process streams that also are substantially homogeneous, this is not the case for heavy hydrocarbon streams such as crude and heavy oils that are similarly dark and inhomogeneous. Raman, for example, has been recognized as being incompatible with these oils due to the phenomenon of auto-absorption by black asphaltene (or carbonaceous) particles of Raman-effect photons. These same particles adversely impact NIR spectroscopy.

A need therefore exists, for an improved system and method for analyzing the content of non-homogeneous petroleum hydrocarbon samples such as crude oil and heavy oils.

SUMMARY

One aspect of the invention includes an apparatus for off-line measurement of the response matrix for a relatively high viscosity, inhomogeneous hydrocarbon mixture such as crude or heavy oils having asphaltenic or carbonaceous particulates therein, which may or may not be liquid at ambient temperature, but which flow at temperatures of 60° C.-80° C. or higher. The apparatus includes a fluid flow path configured to convey a predetermined sample volume of the liquid hydrocarbon mixture continuously in a downstream direction therethrough. A sampling unit is configured to receive the sample volume therein, and to continuously deliver the sample volume to the fluid flow path. The sampling unit includes a temperature control module configured to maintain at least a portion of the sample volume at a predetermined setpoint temperature, a homogenization module configured to distribute the particulates within the sample volume, and a flow control module configured to maintain a substantially constant flow rate of the sample volume as it flows through the fluid flow path. An optical transmission cell is a type of sample cell located within the fluid flow path has an optical path with a predetermined pathlength extending therethrough. A spectrometer is communicably coupled to the transmission cell to transmit and receive radiation. The transmission cell includes collection optics configured to capture and aggregate non-collimated radiation emerging from the optical path, for transmission to the spectrometer. The spectrometer is configured to generate spectra of sample flowing through the optical transmission cell. The apparatus also may include a multivariable model suitable for calculating properties of the liquid hydrocarbon mixture, including crude or heavy oils having asphaltenic or carbonaceous particulates therein, at the predetermined setpoint temperature. A processor is configured to capture and use the sample spectrum in combination with the model to determine properties of the mixture, including the crude or heavy oils having asphaltenic or carbonaceous particulates, while the sample volume flows continuously through the fluid flow path.

In another aspect of the invention, a method of spectroscopic sample analysis includes placing a sample volume within the sample handling unit of the aforementioned apparatus, and actuating the flow control module to maintain a substantially constant flow rate of the sample volume through the fluid flow path. With the temperature control module, the sample volume is maintained at the predetermined temperature as it passes through the transmission cell. With the collection optics, non-collimated radiation is captured and aggregated as it emerges from the optical path of the transmission cell. With the spectrometer, the sample spectrum is generated at a predetermined rate of flow of the sample volume through the optical transmission cell. The processor captures and applies one or a plurality of models to determine a corresponding number of properties for the sample, including the crude or heavy oils having asphaltenic or carbonaceous particulates, while the sample volume flows continuously through the fluid flow path.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
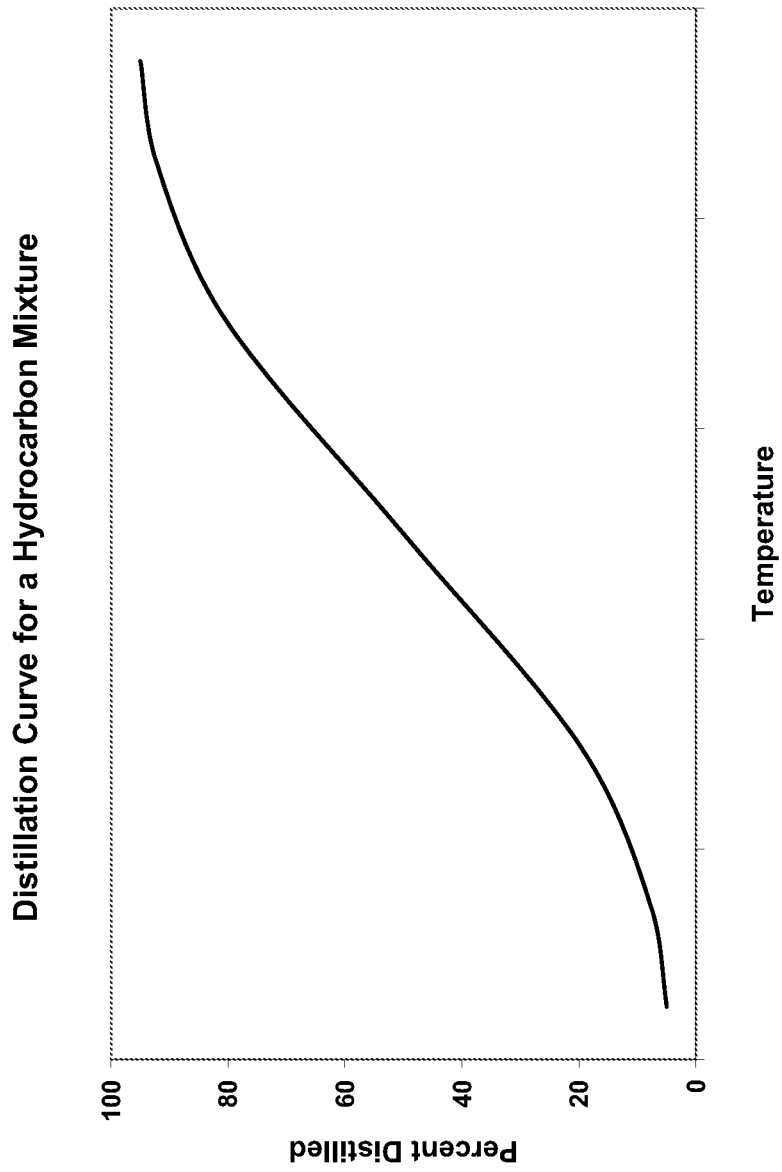
FIG. 1 is a graphical distillation curve for a hydrocarbon mixture of the prior art.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. In addition, well-known structures, circuits and techniques have not been shown in detail in order not to obscure the understanding of this description. The following detailed description is, therefore, not to be taken in a limiting sense, and the scope of the present invention is defined by the appended claims and their equivalents.

General Overview

A method and apparatus is provided for off-line determination of properties or components in a relatively high viscosity, inhomogeneous liquid hydrocarbon mixture in which the liquid hydrocarbon mixture including crude or heavy oils having asphaltenic or carbonaceous particulates therein. Briefly, in a representative embodiment, this approach includes a sampling unit configured to continuously deliver a sample volume to the fluid flow path, including a temperature control module, a homogenization module, a flow control module, an optical transmission cell, a spectrometer, collection optics configured to capture and aggregate non-collimated radiation emerging from the transmission cell, a model or a plurality of models for properties or components of the liquid hydrocarbon mixtures including crude or heavy oils having asphaltenic or carbonaceous particulates, and a processor configured to capture data generated by the spectrometer and to use the data in combination with said model or models to determine a concentration of said properties or components.

Embodiments use multivariate measurement technologies with an off-line, limited sample volume approach, without sacrificing data quality. Particular embodiments employ a near-infrared spectrometer system that overcomes problems encountered when otherwise attempting to analyze samples from refinery hydrocarbon streams including crude and heavy petroleum-derived materials.

In the following description, for purposes of explanation, numerous specific details are set forth in order to provide a thorough understanding of the present invention. It will be evident, however, to one skilled in the art that the present invention may be practiced without these specific details.

As used herein, the terms "heavy oil" and/or "heavy petroleum mixtures" refer to petroleum mixtures having containing asphaltene (or carbonaceous) particles therein, and/or in particular embodiments, petroleum mixtures having an API (American Petroleum Institute) gravity below 22.3 degrees (i.e., below 22.3° API). Examples of "heavy oil" and/or "heavy petroleum mixtures" include vacuum gas oils, bunker fuel, and feeds to fluidized catalytic cracking units. The term "crude oil" is used in the conventional sense and includes but is not limited to blended crudes and crude-oil-like materials such as upgraded bitumen, synthetic crudes, and those derived from tar sands. The terms "pathlength", "transmission pathlength", "measurement pathlength", and/or "optical pathlength" refer to the shortest distance through a liquid sample disposed in a transmission cell. In particular embodiments, the pathlength extends substantially orthogonally to the direction of fluid flow through a transmission cell. As also used in this document, the term "processor" is meant to encompass any suitable computing device including a microprocessor and a computer readable medium upon which computer readable program code (including instructions and/or data) may be disposed, with or without a user interface. The term 'real-time' refers to sensing and responding to external events nearly simultaneously (e.g., within milliseconds or microseconds) with their occurrence, or without intentional delay, given the processing limitations of the system and the time required to accurately measure the data.

Systems and methods embodying the present invention can be programmed in any suitable language and technology, such as, but not limited to: C++; Visual Basic; Java; VBScript; Jscript; BCMAscript; DHTM1; XML and CGI. Alternative versions may be developed using other programming languages including, Hypertext Markup Language (HTML), Active ServerPages (ASP) and Javascript. Any suitable database technology can be employed, such as, but not limited to, Microsoft SQL Server or IBM AS 400.

Referring now to the figures, embodiments of the present invention will be more thoroughly described. Initially, a review of the operation of advanced analyzers/spectrometers is in order. Generally, analyzers generating a response matrix that lends to multivariate analysis of complex sample streams share three common characteristics:

Uniqueness. The correspondence between the response matrix and sample composition is singular because each compound in a mixture contributes uniquely to the aggregate response matrix according toits chemical structure, concentration, interaction with other components in the mixture Temperature dependence. While the chemical composition of the sample determines the fundamental character of the response matrix, temperature typically has a secondary effect. For example, the shape and position of NIR absorption bands vary in ways that are subtle but consistent and measurable at temperatures differing by one degree Celsius or less.

Figure 2:
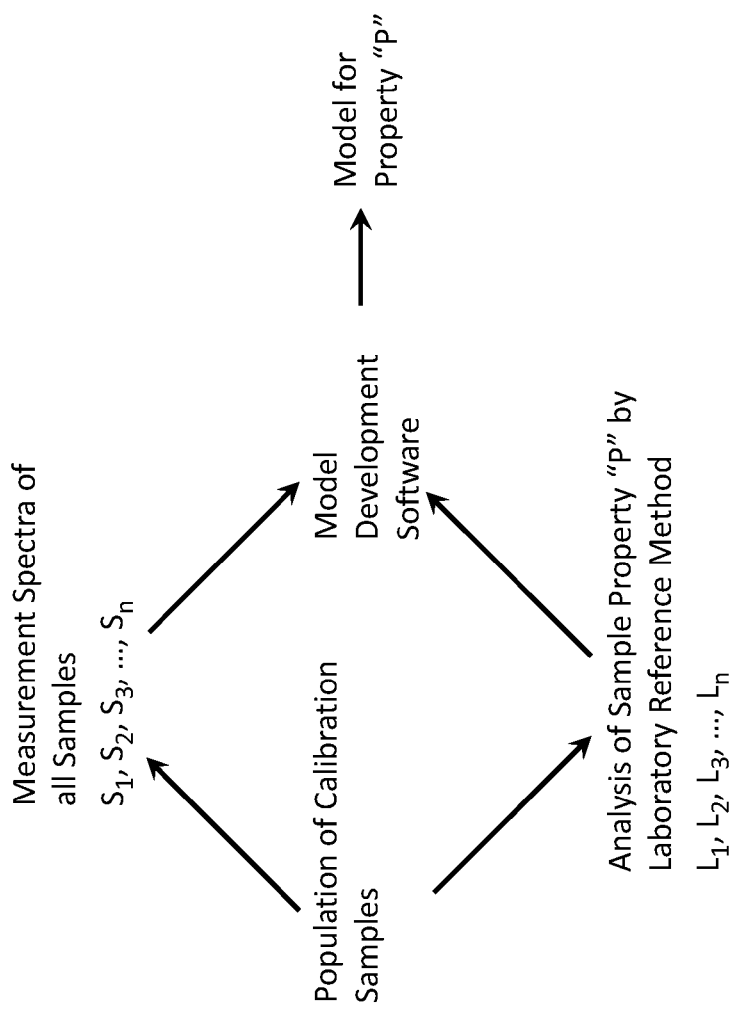
FIG. 2 is a functional diagram of a scheme for model development that may be used with embodiments of the present invention.
Figure 3:
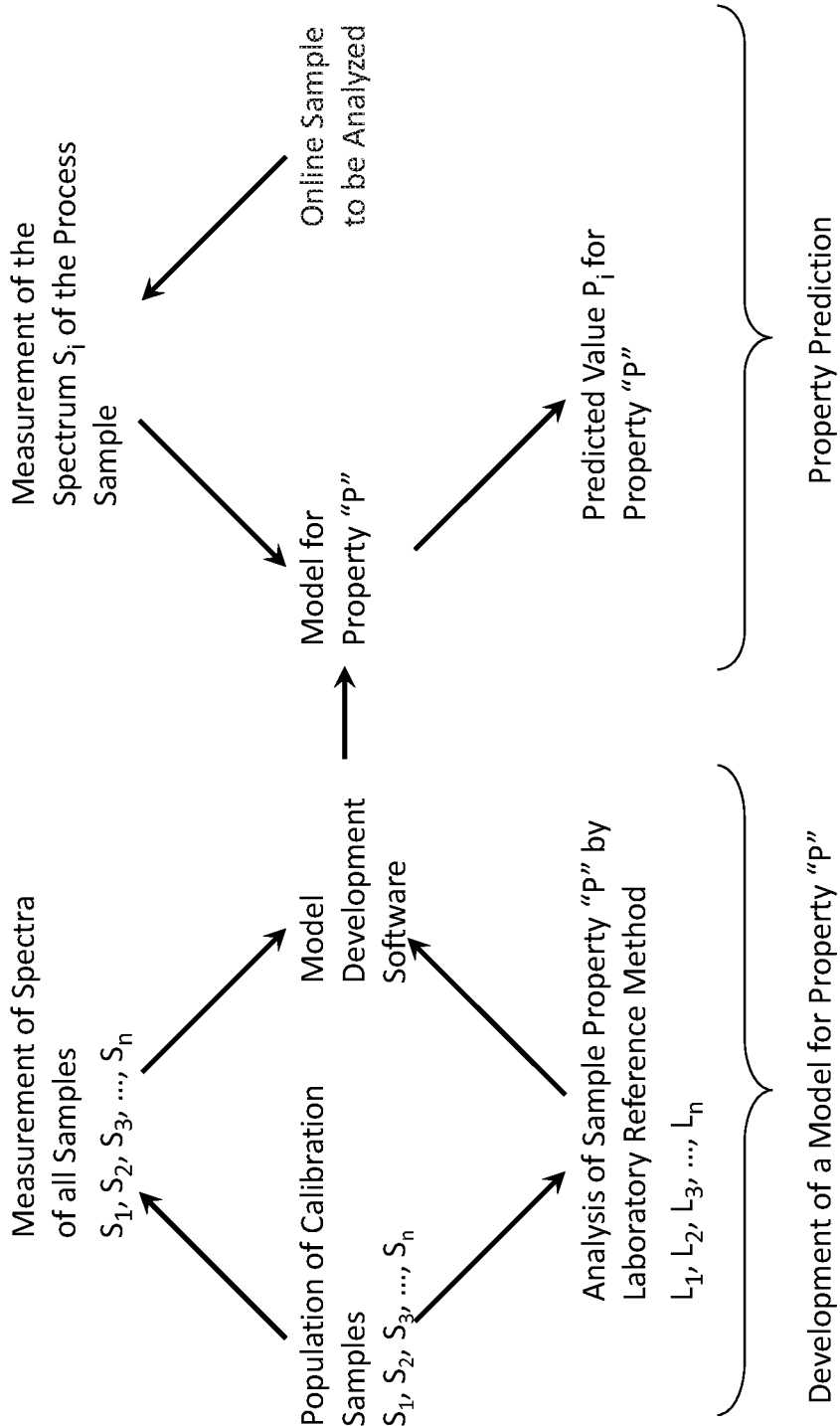
FIG. 3 is a functional diagram of a scheme for property prediction through application of a property model, that may be used with embodiments of the present invention.

Referenced (secondary) method. A multivariate mathematical model relates the response matrix to the desired property value that generally can be determined in the laboratory in accordance with a primary test method defined by an organization or authority recognized by the industry. Multivariate statistical modeling techniques (common algorithms include Partial Least Squares (PLS) and Principal Component Regression (PCR)) extract information distributed across the entire spectrum for correlation with primary test method results, in a manner such as shown in FIG. 2. The application of the resultant calibration models to the measured spectrum of a sample yields values for those properties, such as shown in FIG. 3.

In particular applications, the response matrices of a sample may be grossly similar but measurably different at two different temperatures, e.g. 25.0° C. and 26.0° C., and a particular characteristic therefore may be defined in a way that encompasses both composition and temperature. But as a practical matter, controlling the latter minimizes and/or simplifies the task of developing reliable multivariate models that relate properties of interest to samples' response matrices. In particular embodiments, temperature is controlled to facilitate the capture of response matrices for a relatively wide range of populations of crude oil, heavy oil, or other heavy hydrocarbons.

Figure 4:
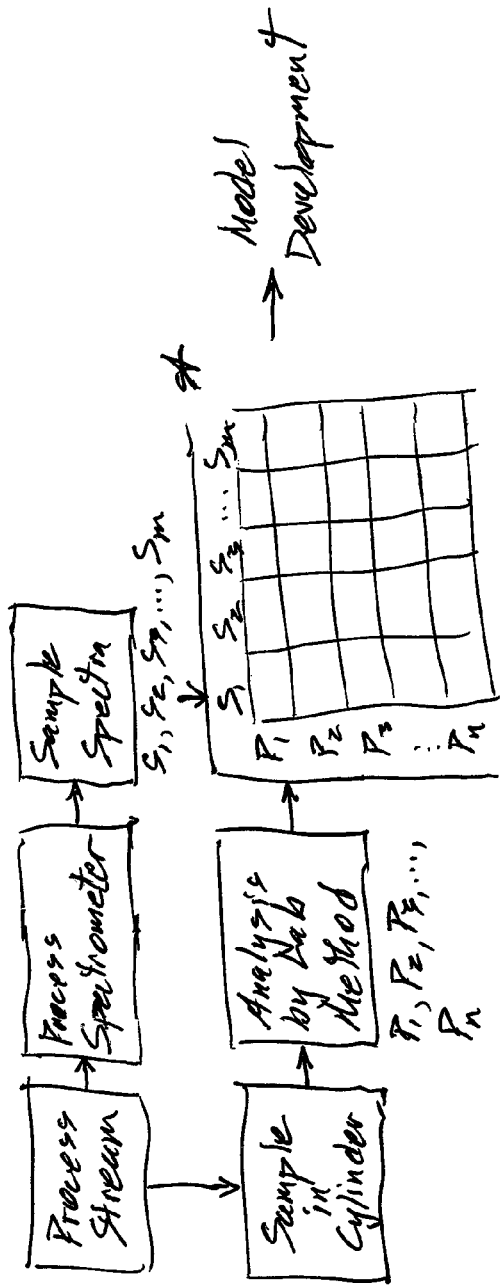
FIGS. 4 and 5 are functional diagrams of a data collection schemes that may be used with the model development and property prediction schemes of FIGS. 2 and 3.
Figure 5:
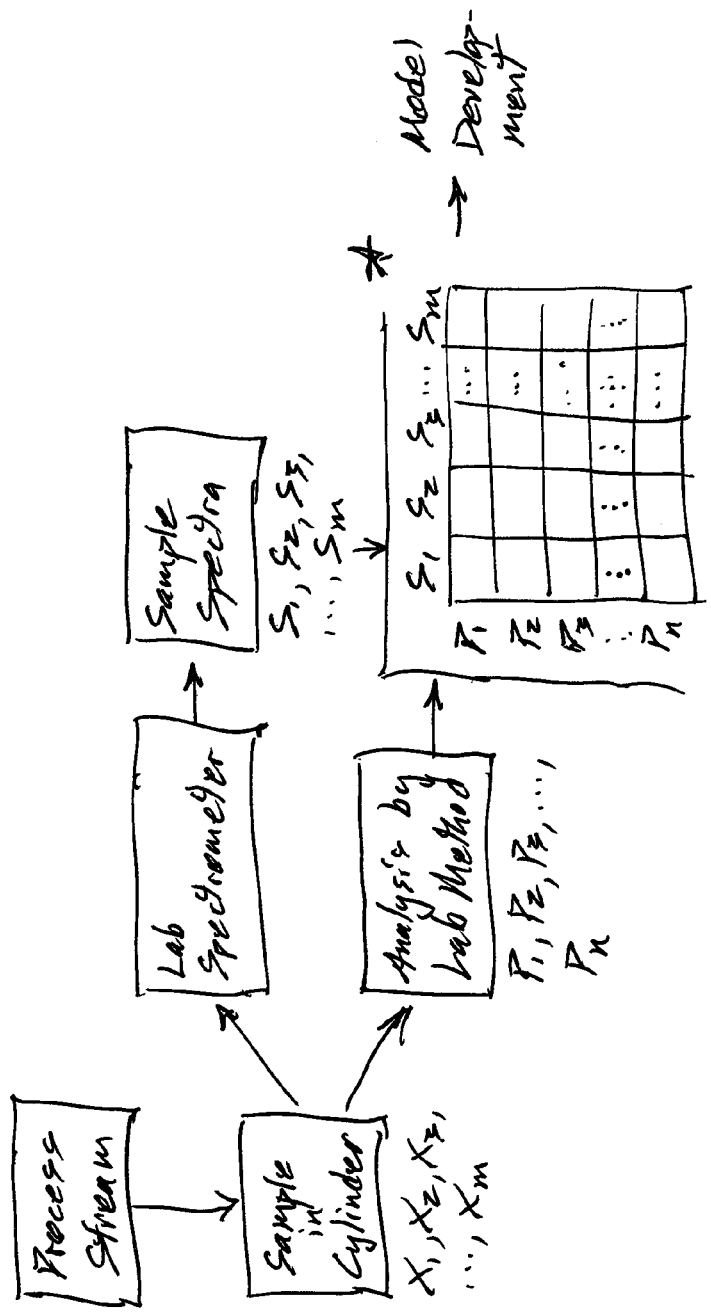

Turning now to FIGS. 4 and 5, exemplary paradigms (Data Collection Schemes I and II) are shown for developing calibration models that relate the response matrices of samples to values for properties or components of light hydrocarbon streams, i.e. motor fuels and the components from which they are prepared. In one case, an online spectrometer measures spectra of the selfsame process samples that are captured physically in vessels and subsequently delivered to the laboratory for analysis of the properties of interest by the primary test methods (FIG. 4). Alternatively, samples captured in a suitable sampling vessel may be delivered to the laboratory where their spectra and the corresponding reference values are measured (FIG. 5). In this case, the spectrometer used may be functionally equivalent to one installed online, permitting direct transfer to the latter of the resultant calibration model.

The success of both approaches depends on the integrity in sampling and sample handling, along with the correct spectral measurement and data handling. Thus, both Data Collection Schemes rely on the composition of the sample in the vessel delivered to the laboratory for analysis by primary test methods being the same as that of the sample for which the spectrum was measured, whether online or in the laboratory. In addition, the portion of sample from the vessel that is analyzed in the laboratory needs to be representative of the vessel's entire content, and in the case of Scheme II (FIG. 5), this same condition applies to the sample presented for spectral measurement.

Data Collection Schemes I and II may be practiced routinely and successfully to support the development of calibration models for advanced analyzers for analysis of hydrocarbon streams that are relatively light (e.g., in which a majority of the components distill at relatively low temperatures), common examples being gasoline and diesel; the components from which they are blended; and naphtha feed to olefin crackers. However, the paradigm described in FIG. 5 becomes impractical for at least three reasons for many heavy petroleum mixtures, crude oil being perhaps the most important example.

One reason that the FIG. 5 approach has not been practically used in the prior art, is that unlike refined petroleum products, crude oil is not homogeneous and tends to stratify. Another reason is that the viscosity of many varieties of crude oil is so high that samples do not flow readily at room temperature and therefore it is generally desirable to heat crude oil to 60° C.-80° C. or higher, to facilitate sampling. In addition, handling at elevated temperatures tends to compound the difficulty of maintaining sample integrity, since even heavy crudes have light components like pentanes and hexanes, whose isomers boil at temperatures at or below 36° C. and 69° C., respectively. Thus, a sample handling methodology that permits realization of Data Collection Scheme II should not only heat the sample to facilitate flow into a measurement cell, but should also maintain sample homogeneity and prevent loss of light components. However, heating exacerbates problems of stratification and containing volatile components.

The instant inventors have recognized that while controlling to ±5° C. is relatively easy, the greatest sensitivity in calibration models is achieved when temperature is controlled to ±1.0° C. or tighter. They have also realized that the same components that settle out from a stationary sample also have optical effects that impact the quality of spectra measured by optical spectroscopy methods such as Raman or NIR. It was recognized that Raman is generally unsuitable for analyzing crude and heavy oils that are similarly dark, due to the phenomenon of autoabsorption by black asphaltene (or carbonaceous) particles of Raman-effect photons. These same particles impact NIR spectroscopy, since instead of collimated output 50 from a sample cell 20 (FIG. 6A), the particles in crude oils and heavy hydrocarbons tend to scatter the rays of (NIR) light used to interrogate the sample, to generate a non-collimated output 52 (FIG. 6B). This phenomenon tends to generate wavelength-dependent distortion of the baseline (FIG. 7). This effect increases as wavelengths decrease, making the sample effectively opaque in some spectral regions commonly used to analyze relatively light, clear hydrocarbons.

Representative Embodiments

Data Collection Scheme I (FIG. 4) presents few impediments for acquiring spectra of samples because of the ability to design an online sampling system that tightly controls sample temperature while preventing stratification and loss of volatiles. Yet, despite working well, the Scheme may be impractical for use in acquiring spectra for a diversity of crude oil samples off-line, e.g., for applications in which use of an online analyzer may be impractical and/or cost prohibitive, such as involving samples from storage tanks, pipelines, cargo ships, etc. Therefore, embodiments of the present invention have been developed to address issues described above, to enable the effective realization of Data Collection Scheme II for crude oil and the like.

Figure 8:
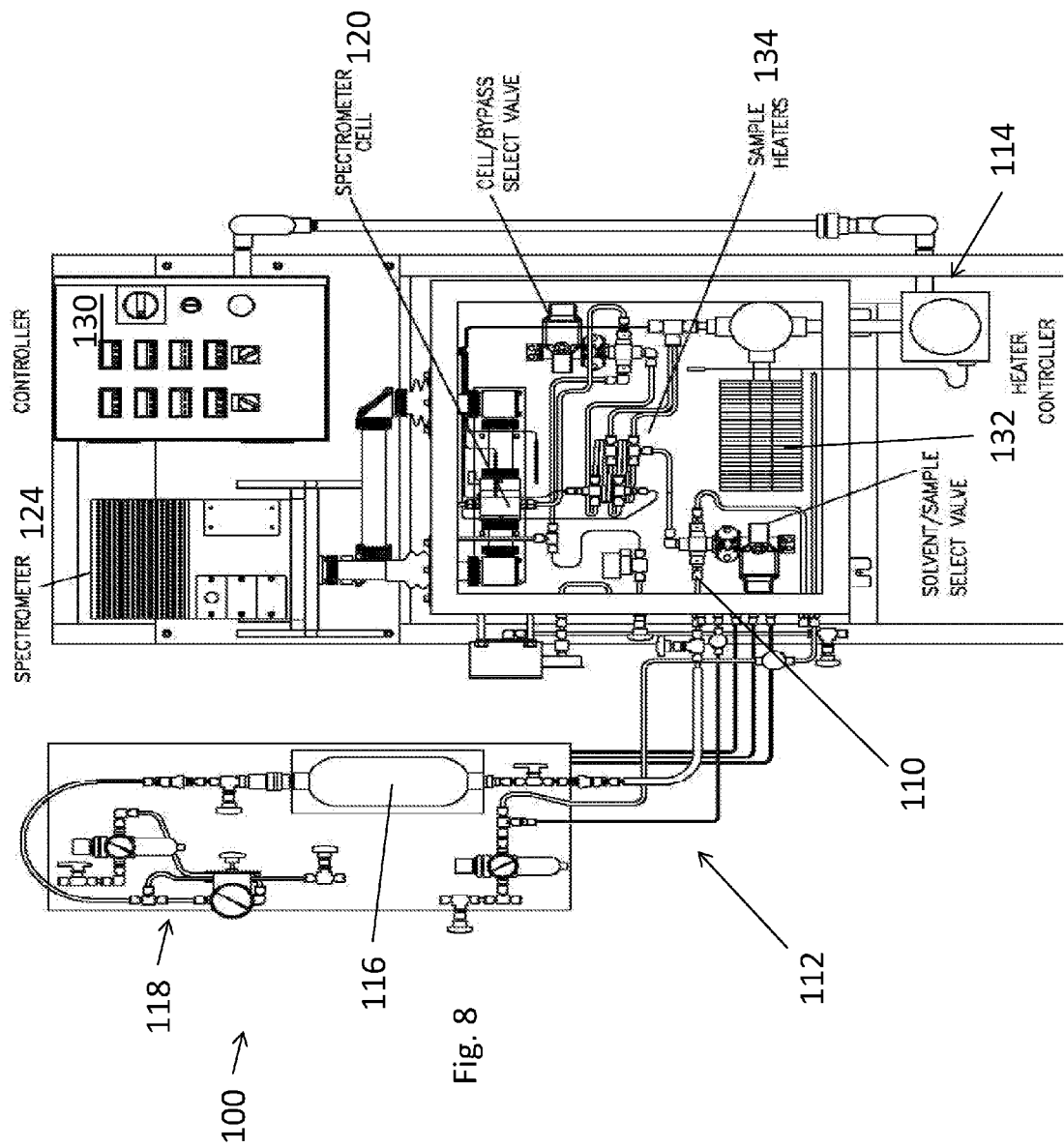
FIG. 8 is a schematic diagram of an embodiment of the present invention.

Turning now to FIG. 8, an embodiment of the present invention shown as analyzer 100, is configured for off-line concentration determination of components in a relatively high viscosity, inhomogeneous liquid hydrocarbon mixture including crude or heavy oils having asphaltenic or carbonaceous particulates therein, which liquid hydrocarbon mixture has properties or components whose values are unknown. Analyzer 100 includes a fluid flow path 110 configured to convey a predetermined sample volume of the liquid hydrocarbon mixture continuously in a downstream direction therethrough. A sampling unit 112 is configured to receive the sample volume therein, and to continuously deliver the sample volume to the fluid flow path. Sampling unit 112 includes a temperature control module 114 configured to maintain at least a portion of the sample volume at a predetermined setpoint temperature, a homogenization module 116 configured to distribute the particulates within the sample volume, and a flow control module 118 configured to maintain a substantially constant flow rate of the sample volume as it flows through the fluid flow path. In particular embodiments, the temperature control module includes an actively controlled heat exchanger disposed downstream of the homogenization module, and upstream of the spectrometer. The heat exchanger, e.g., in combination with the controller, is configured to maintain at least the portion of the sample volume within the transmission cell, within about 1 degree C. of the predetermined setpoint temperature. It should be noted that in many applications, maintaining the sample temperature within about 1 degree C. has been shown to facilitate desired accuracy of results, while in other applications, a wider range of sample temperatures, e.g., within about 2 to 5 degrees C., may be used without departing from the scope of the present invention.

As also shown, an optical transmission cell 120 is disposed within the fluid flow path, the transmission cell having an optical path with a predetermined pathlength L (FIGS. 9, 10) extending therethrough. A spectrometer 124 is communicably coupled to the transmission cell 120, to transmit and receive radiation to and from the transmission cell. The transmission cell 120 includes collection optics 126 (FIGS. 9, 10) configured to capture and aggregate non-collimated radiation emerging from the transmission cell, for transmission to the spectrometer. In particular embodiments, spectrometer 124 is configured to generate sample spectra at a rate of at least once per milliliter of flow of the sample volume through the optical transmission cell, though substantially any data rate may be used for various applications.

Analyzer 100 also may include one or a plurality of property models for liquid hydrocarbon mixtures, including crude or heavy oils having asphaltenic or carbonaceous particulates therein, at one or more predetermined setpoint temperatures. The model(s) may be stored on a non-transitory computer readable medium, as defined herein. A processor, such as associated with controller 130, is configured to capture data generated by the spectrometer 124, and to use the data in combination with the model to determine a concentration of the components within the sample volume as it flows continuously through the fluid flow path.

Additional details associated with various embodiments of the invention will now be described as they relate to the sampling, data acquisition, optics, and spectrometry.

Sampling

The sampling unit 112 may include a homogenization module 116 of any desired capacity, e.g., anywhere from about 20 to 2200 mL or more. In particular embodiments, module 116 is capable of receiving a sample volume within the range of about 300-400 mL up to about 2200 mL or more. In particular embodiments, the capacity should be at least sufficient to help ensure that the sample delivered into the analyzer is representative of the process stream from which it was obtained. A capacity within a range of about 500 mL-1000 mL may be desirable for many applications. As shown, module 116 may be a cylinder fitted with inlet and outlet shutoff valves. In addition, module 116 may be configured for being filled online, such as shown in FIG. 11, e.g., via sample transfer lines 140, to a process stream through which the liquid hydrocarbon mixture flows.

In particular embodiments, the module 116 may be oriented for analysis, e.g., with an outlet shutoff valve at the bottom, with a transfer line connected to the outlet valve, forming a portion of fluid flow path 110. An inlet valve may be coupled to flow control module 118, which in the embodiment shown, includes a gas line that applies a head pressure of suitable magnitude to displace sample from the sampling vessel into the main analyzer enclosure. The gas is preferably an inert gas such as nitrogen. Optionally, the gas may be helium, which both has limited solubility and readily stratifies in gas phase to maximize the partial pressure of light HCs immediately over the surface of the liquid sample, thereby minimizing the their loss from the bulk liquid phase to maximizes sample integrity.

Optionally, module 116 may be wrapped in a heated jacket and the sample transfer line may be heat traced as appropriate to ensure the ready flow of samples whose viscosity may otherwise become unacceptably high at temperatures between ambient and the analysis setpoint temperature. It is noted that the objective of such heating is not necessarily temperature control, but rather, viscosity management.

Figure 12:
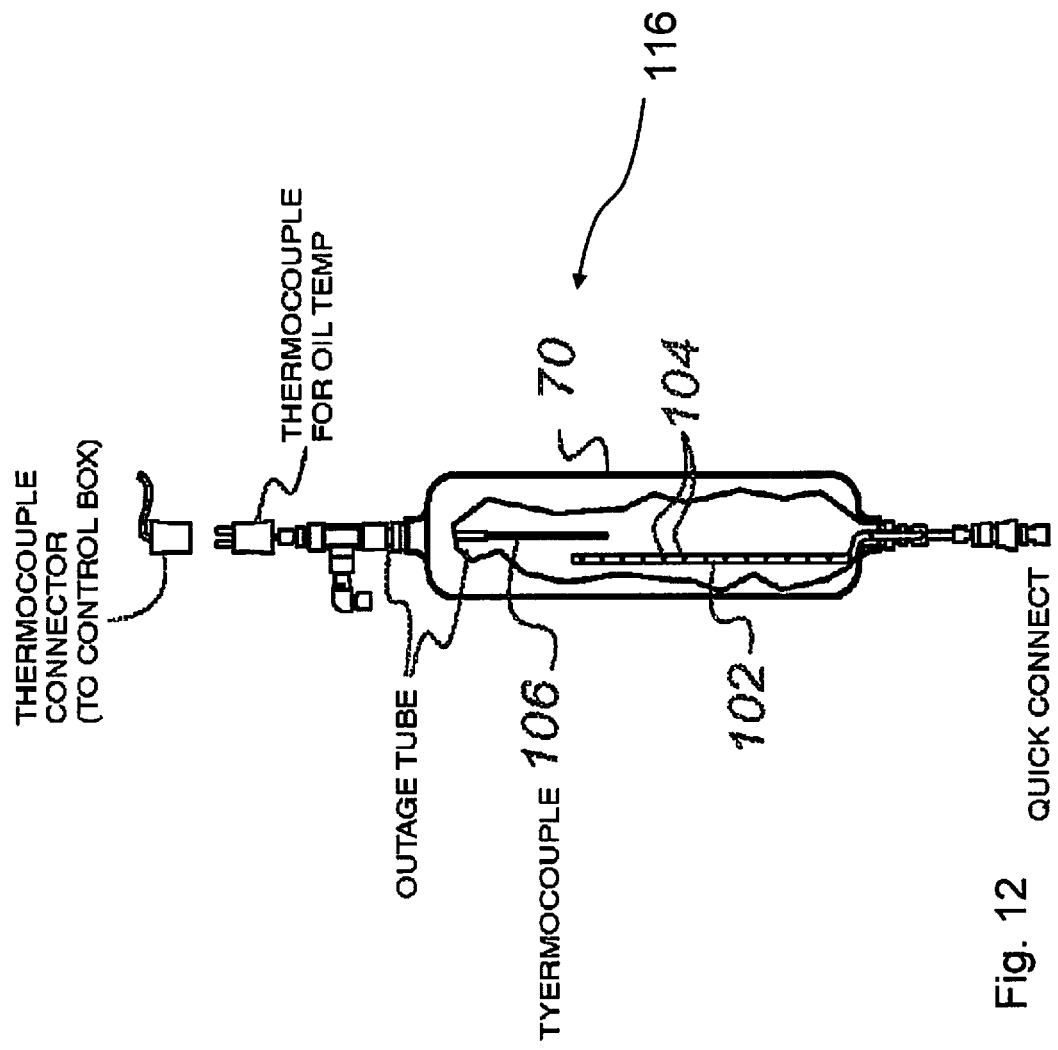
FIG. 12 is a schematic view, on an enlarged scale, of components usable with the embodiment of FIG. 8.

Turning now to FIG. 12, in particular embodiments, to help maximize representative sampling, homogenization module 116 may include a cylinder 70 having a drain tube 102 that extends longitudinally therein, and which has holes spaced at intervals along its length, such as disclosed in U.S. Pat. No. 7,667,461 entitled SAMPLE ANALYZER AND SAMPLING SYSTEM (hereinafter, the "'461 patent"), which is fully incorporated herein by reference. Under the head pressure applied by flow control module 118 (FIG. 8), sample flows simultaneously into holes in the drain tube 102 that are below the top of the liquid column. For example, as shown, cylinder 70 may be provided with a tube 102 attached to its lower outlet. The tube may be generally long enough to extend along at least 50 percent or more of the length of the cylinder. A plurality of holes (orifices) 104 are spaced along the length of the tube 102 to permit sample to flow into the tube 102 from multiple levels in cylinder 70, i.e. to facilitate "distributed sampling." The spacing and/or diameter of the holes 104 may be varied from bottom to top to help maintain the flow rate of sample displaced through each hole nominally constant, e.g., regardless of the total amount of sample remaining in the cylinder. A hole 96 (not shown) may be provided at the base of tube 102 to help ensure that sample is displaced in a quantitative and representative fashion. Cylinder 70 may be provided with a temperature sensor, such as a thermocouple 106 as shown, which may be used by temperature control module 114 to help maintain desired sample temperatures.

Figure 13:
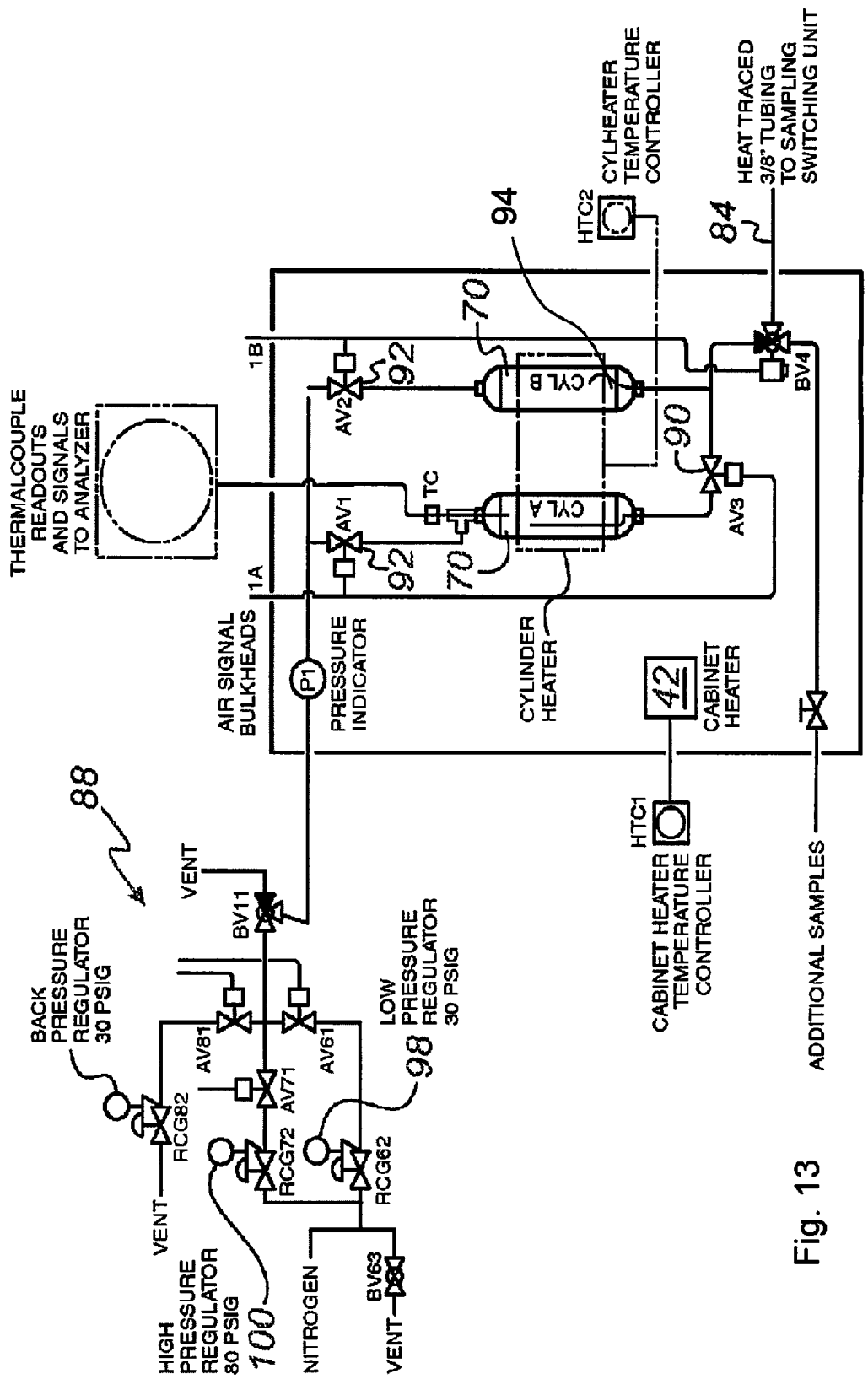
FIG. 13 is a view similar to that of FIG. 12, of alternate components usable with the embodiment of FIG. 8.

In alternate embodiments, a displacement mixing approach may be used, e.g., in which sample is displaced from "Cylinder A" (70) into "Cylinder B" (70') prior to delivery into the analyzer system, as also disclosed in the '461 patent. For example, as shown in FIG. 13, mixing may be accomplished by pressurizing cylinder A (70) using gas from gas supply 88, and opening the valve 90 to permit displacement of sample into cylinder B (70'). As best shown, a sample inlet tube 94 is provided to deliver sample to the interior of cylinder B (70'). A proximal end of tube 94 is fastened to the cylinder inlet. The tube extends from the proximal end toward the distal end, generally curving radially outward towards the periphery of the cylinder. In particular embodiments, the curvature is configured so that the distal end of tube 94 is substantially tangent to the inside surface of the cylinder on a plane substantially perpendicular to the cylinder axis, approximately 10-50 percent of the distance from the bottom to the top of the cylinder as shown. As a result, sample entering cylinder B (70') does so in a direction substantially perpendicular to the cylinder axis and flows along the inside surface of the cylinder, creating a radial flow facilitating the mixing of sample.

Prior to injection, Cylinder B may be purged with an appropriate, dry gas, e.g., from gas supply 88. As mentioned hereinabove, helium may be preferred for some applications, as some processes are sensitive to nitrogen or oxygen; and since helium is substantially insoluble in liquids, its use tends to eliminate off-gassing and the formation of bubbles upon reduction of sample pressure, which might otherwise occur in the event a more soluble gas were used for the same purpose.

As sample fills cylinder B (70'), it compresses the gas therein (since valve 92 has been closed). (Depending on the pressure applied to Cylinder A, a pressure relief valve (not shown) may or may not be required to permit venting of the gas through the valve 92 at the top of the cylinder B and to facilitate the aforementioned displacement of sample into Cylinder B through the tube 94.) Because materials such as crude oil contain volatile components that boil below 80° C. at ambient pressure, adequate pressure should be maintained to prevent boiling/distillation of these components during filling of cylinder B. Additionally, the initial flow rate should be relatively slow until the distal end of the inlet tube is submerged so as to minimize the distribution of sample on the inside surface of the cylinder above the level of the sample. To accomplish this, gas supply 88 may use dual-regulators, e.g., including both low and high pressure regulators 98 & 100, respectively, to apply low pressure initially, and subsequently provide higher gas pressure to produce higher flow rates as may be desired to facilitate mixing and to overcome pressure build-up within cylinder B.

Since sample initially filling cylinder B (70') may not be representative of the bulk sample in cylinder A (70), the inlet tube 94 may be provided with a relatively small hole 96 (FIG. 5) near its proximal end just inside the cylinder to facilitate upward displacement of sample that may otherwise collect at the bottom of cylinder B (e.g., below the distal end of the inlet tube 94). The geometry of the distal end of the inlet tube 94 may also be formed as desired, such as in the form of a nozzle, to increase the velocity of sample entering cylinder B therefrom, and to create back-pressure sufficient to promote desired levels of flow through the hole 96.

Referring back to FIG. 8, as discussed above, in various embodiments, at least a portion of the sample volume is maintained at a predetermined setpoint temperature. In a representative embodiment, this may be accomplished by a temperature control module 114, which may include a conventional air bath heater 132 disposed within an insulated cabinet. This heater 132 provides a nominally stable thermal environment for the various elements of the analyzer system inside of the enclosure, including various valves, fittings and tubing, etc. In this embodiment, heater 132 is not the primary means for controlling sample temperature, but is used to help control the viscosity of the sample as discussed hereinabove and to provide a baseline from which the setpoint temperature may be reached using sample heater(s) 134.

As shown, one or more sample heaters 134 provide for temperature control of flowing sample, such as by use of any number of conventional fast-response thermal conditioning devices.

In this regard, it should be recognized that the distribution amongst energy levels associated with chemical bonds in constituent sample molecules is temperature-dependent. Molecular spectra vary in sometimes subtle but measurable ways as a function of this temperature-dependency. Property modeling based on measured sample spectra needs to either compensate for such effects, or alternatively, maintain the sample at a substantially isothermal temperature.

Some embodiments may provide for temperature compensation by employing one or more models of various sample materials at a variety of temperatures. These models may then be used by controller 130, in combination with temperature data for the sample as it passes through the transmission cell 120, for analysis. These embodiments may use one or more temperature detectors configured to generate temperature data for the sample volume as it flows through the sample cell. The controller (e.g., processor) 130 may be configured to capture data generated by the spectrometer and the one or more temperature detectors, and to use the data in combination with the model(s) to determine a temperature compensated concentration of the components in the sample volume.

However, for many applications, such as described hereinabove, it may be desirable to maintain/control the sample temperature within narrow limits, so that as a practical matter, the sample is isothermal. This approach substantially eliminates the complicating effects of temperature on modeling. A difficulty with this approach is maintaining such precise temperature control as the sample flows through the transmission cell 120, which in particular embodiments, is maintained at a flow rate within a range of about 20-60 mL/min.

Such temperature control may be provided by one or more sample heater 134 in the form of an actively controlled, heat exchanger with a relatively low thermal mass, e.g., having a thermal mass less than that of the sample fluid therein. Examples of such heat exchangers may include coil and cable heaters, flexible heaters, radiant heaters, induction heaters, microwave heaters, tubular heat exchangers, shell and tube heat exchangers, spiral tube heat exchangers, plate and frame heat exchangers, and combinations thereof.

In one exemplary approach, such temperature control is provided using a two-stage, coarse/fine temperature conditioning approach. A first stage heater conditions the sample to a temperature approximately 10° C. lower than the predetermined set point temperature, while a second stage conditions to ±1° C. of the analysis setpoint temperature. Particular embodiments are capable of maintaining setpoint temperatures anywhere within a range of about 35 to 100 degrees C. In practice, a measurement setpoint temperature of about 80.0° C. facilitates sampling of crude and heavy oil samples having API gravity values as low as 12-14 degrees. A higher analysis setpoint temperature may be appropriate if samples of yet lower API gravity were to be analyzed regularly.

Although not limited to this approach, in an exemplary embodiment, the two stages of heaters 134 may be of substantially identical design, and running most of the length of each tube is an electric heating element in the form of a flexible cable, with a temperature sensor disposed at approximately the midpoint thereof. The temperature sensor may be used both for temperature control and to guard against inadvertent overheating, such as in the event of a stop-flow condition.

Heating the sample as it flows the length of the tube(s) tends to reduce both the maximum temperature required to heat the sample to the target temperature and the amount of thermal energy per unit volume of flowing sample. This in turn tends to reduce or eliminate two effects that may otherwise occur: coking of sample on the heating element; and volatilization of lighter components.

In a non-limiting example, the tube(s) is metal, having a length in the range of about 0.25 m to 2.5 m (nominal length 1.2 m (4 feet)), with an outside diameter of ¼" to ⅜". The diameter of the heating cable is approximately ⅛". It is noted that the tube size is selected to help minimize internal dead volume and associated sample loss during initiation of the analysis; minimize the thermal mass of sample that needs to be heated at a given instant; minimize the pressure drop for the sample liquid across the length of the device; and maximize the surface-to-volume ratio to aid in thermal equilibration between sample, tubing, and the interior of the sample enclosure.

Temperature control module 114 includes a programmable temperature controller that regulates power to the heaters 134 by feedback from an RTD at the outlet of each stage (and/or at the midpoint thereof, as discussed above), before the sample flows to the measurement cell. Moreover, during analysis initiation, a valve between the outlet from the heater and the inlet to the measurement cell may divert sample that has not been equilibrated to the setpoint temperature. This volume that bypasses the cell prior to analysis is small, typically between 25 and 50 mL. This bypass helps to prevent cooling of the cell by the sample during analysis initiation. The valve may then redirect flow back to the measurement cell once the sample temperature is within the desired tolerance of the predetermined setpoint, e.g. ±1° C.

It should be recognized that while a two-stage heating approach may be desired for many applications, a single stage device may be used in some applications. It is expected, however, that the strategy of pairing coarse preheating with final temperature tuning, accomplished by means of separate devices connected in series, may provide for more precise maintenance of sample temperature.

Sample flow rate may be controlled, using feedback from a flow meter in the fluid flow path 110 to regulate the head pressure provided to sample cylinder 116 by flow control module 118. In addition, or in the alternative, positive control of flow may be provided e.g., by a proportioning valve or a positive-displacement pump downstream from the measurement cell.

Data Acquisition

Problem: Stratification. Certain types of crude oil have a propensity to stratify in relatively short time frames. For example, a liter of certain crude oils may begin to show clear evidence of stratification after only 10-20 minutes at 80° C. Thus, the possibility exists that some amount of stratification might occur in the sample container during the span of 25 minutes that 1 L of sample flows into the analyzer at a rate of 40 mL/min. Notwithstanding the sampling technique described above, whereby sample flows from the sample cylinder through holes along the length of a drain tube inside, the possibility exists that the composition of the sample in the measurement cell at any given instant will be measurably different than at any other time during the 25 minute sampling interval.

Solution: Continuous Data Acquisition. Embodiments of the present invention address this problem by recording spectra substantially continuously (i.e., repeatedly at a rate of at least once for every few milliliters) as the sample flows through the measurement cell for the full duration of the sampling interval. Thus, following analysis initiation, the responses measured for the flowing sample are stored and subsequently averaged to obtain a spectrum representing the aggregate of the sample material that flowed through the measurement cell from the sample cylinder.

Benefit: Signal Averaging. As is the case with other types of signal averaging, this technique minimizes the effect of instantaneous variations in sample composition related to sample inhomogeneity (stratification) during sampling. Additionally, the resultant spectrum will typically represent 10-20 minutes of data acquisition, and signal averaging means that the absolute noise level in the final sample spectrum will be relatively low. For example, if a sample spectrum were normally obtained as the average of multiple, individual spectra obtained during a one minute interval, then the noise in a sample spectrum obtained by averaging spectra acquired during a 16 minute interval would be lower by a factor of four (square-root of 16).

Benefit: Spectral Quality Control. The substantially continuous acquisition of sample spectra allows each individual spectrum, e.g., measured on the time frame of seconds, to be individually compared with all others in the spectral data set measured on a particular sample. Given that bubbles perturb spectra in ways that are distinct, criteria may be applied to reject such spectra. Conversely, the population of spectra deemed to be otherwise acceptable may exhibit a net variance that is characteristic of inhomogeneity in the sample. Therefore, typical variance levels for data sets may be identified and defined to provide a gauge for identifying issues with sampling or sample quality—and for determining whether a sample spectrum is reliable.

Optics

Beginning in the early 90s, near-infrared (NIR) spectroscopy moved from the laboratory to the process due to at least three factors: the rapid advancements in low-cost computing power; the proliferation of user-friendly chemometric modeling programs; and the proliferation of near-infrared spectrometer manufacturers offering process analyzer systems. Spectroscopists in the petrochemical and refining industries began to broadly implement NIR analyzers for real-time, online measurement of properties that hitherto could only be measured by technicians in the laboratory. In many cases, the models could be developed to simultaneously measure multiple properties in a single stream, blended gasoline being a common example, with NIR spectroscopy offering the potential to measure perhaps a dozen properties including research and motor octane number (RON and MON), total aromatics, total olefins, percent benzene, distillation points, vapor pressure, and density.

As mentioned above, analyzer manufacturers and third-party manufacturers of sampling cells generally directed their marketing, scientific, and engineering resources toward development of tools for measuring clear hydrocarbon streams. Such streams generally represented applications where technical issues of sampling and optics, spectroscopy and modeling all could be addressed straightforwardly to provide a commercially viable measurement. Consequently, optical designs of NIR sampling cells presupposed clear, light hydrocarbon streams and were generally configured optically to impinge the sample with a collimated beam, such as discussed above with respect to FIGS. 6A and 6B. Thus, whether coupled to the spectrometer by fiber optics or optically coupled to the spectrometer in a manner that obviates the need for fiber optics, these commercial NIR spectrometer systems are optimized to measure clear hydrocarbon samples.

As also discussed above, by conventional wisdom, NIR spectroscopy was unsuitable for analysis of "dark" petrochemical streams, a view reinforced by the numerous NIR manufacturers around the world. While broadly offering their technology to measure gasoline, diesel, and similarly light hydrocarbon streams, they conspicuously did not promote corresponding offerings to measure dark, heavy process streams such as crude oil, despite the fact that knowledge of crude oil properties generally has far greater import to the efficient operation of refineries.

In one sense, this view is accurate: due to the predominant use of fiber optics, NIR spectrometry of clear liquids measures overtones occurring at wavelengths shorter than 2000 nm, the nominal optical cutoff of conventional "NIR-grade" quartz or silica fiber optics. Due to the relative weakness of these overtones, cell pathlengths of 2 mm and greater are used to obtain the desired peak absorbance values. The use of higher overtones, whose intensities are weaker still, requires pathlengths that may be as large as 5-10 mm.

Figure 6A:
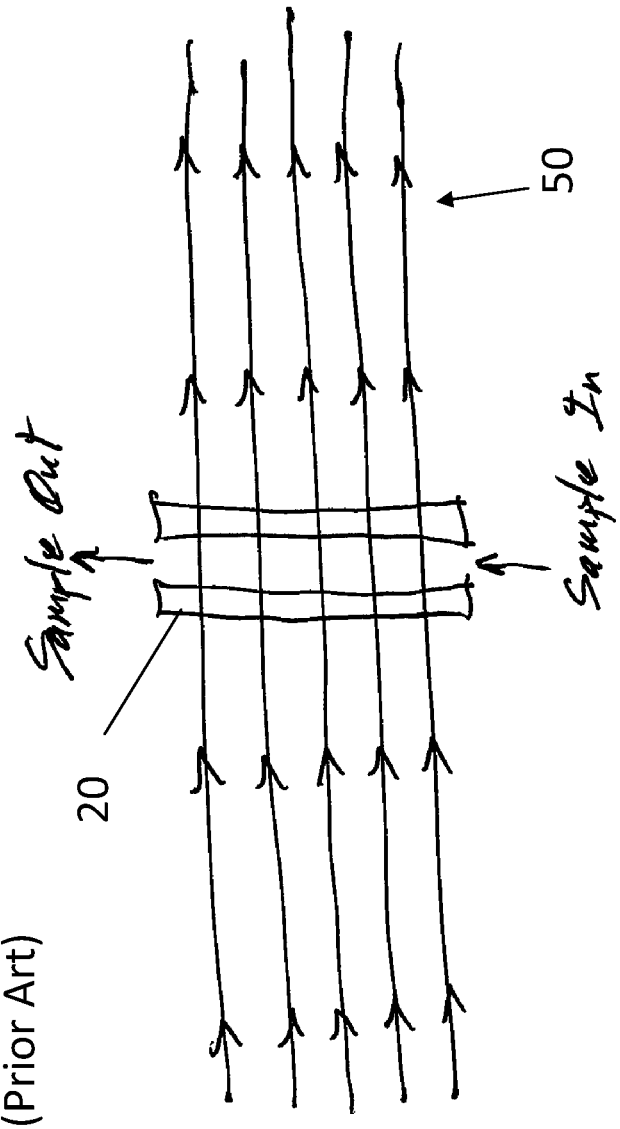
FIGS. 6A and 6B are diagrammatic views showing aspects of spectrometer operation of the prior art.
Figure 6B:
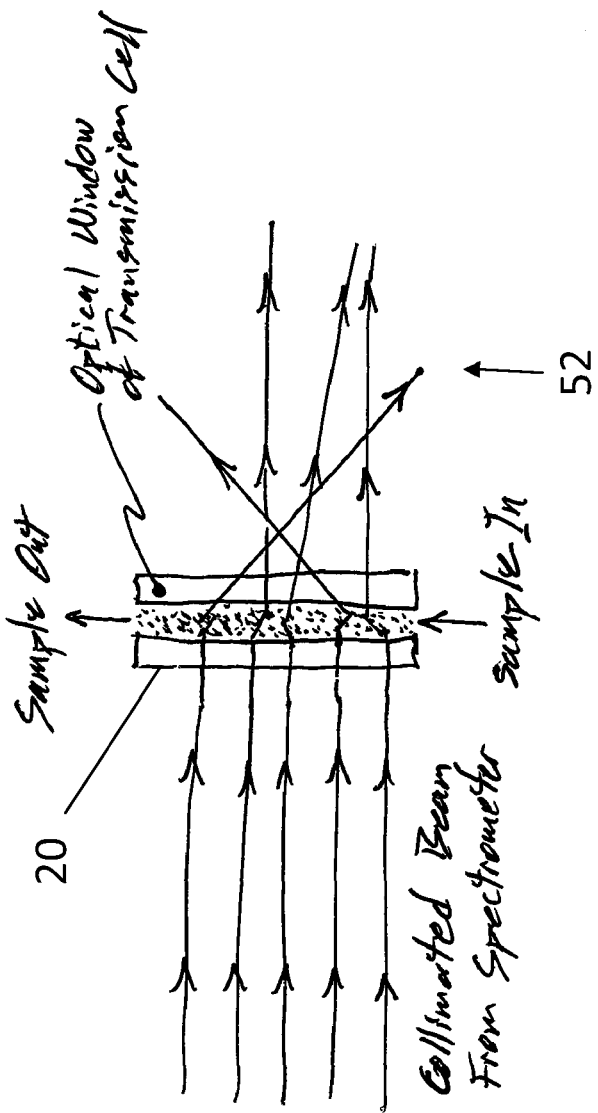
Figure 7:
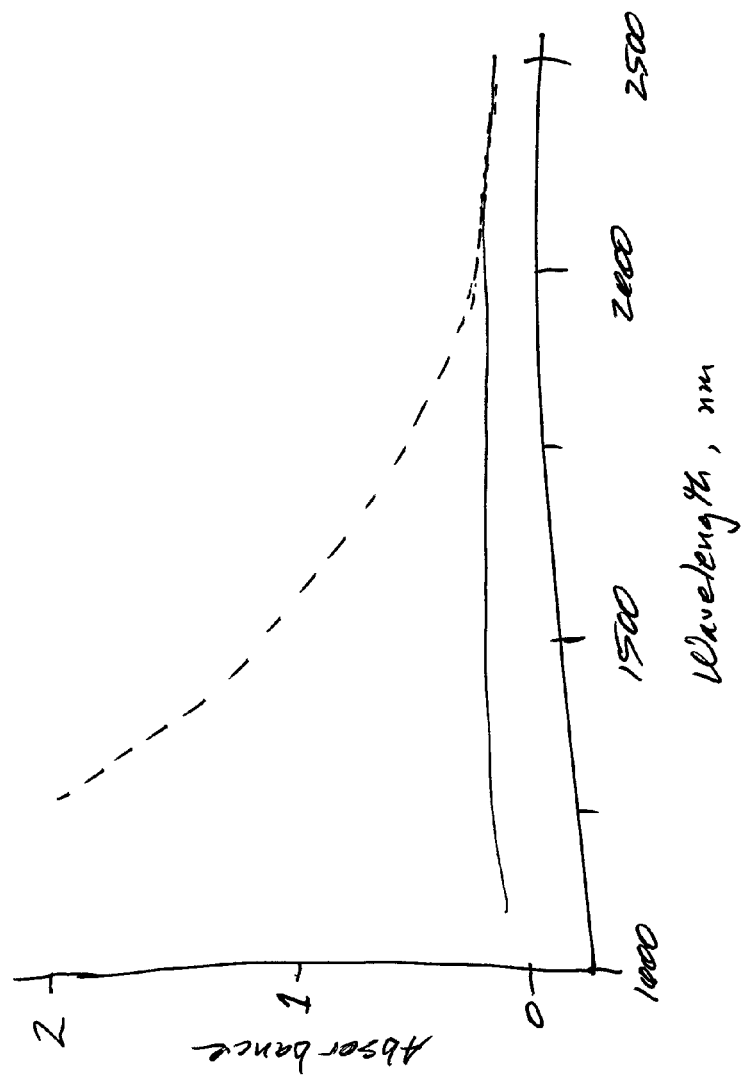
FIG. 7 is a chart depicting the wavelength-dependent distortion of a sample's spectral baseline caused by particulates, demonstrating aspects of the present invention.

The measurement of NIR spectra for clear hydrocarbons at any appropriate pathlength is relatively straightforward, as they readily transmit the collimated NIR beam to without appreciable distortion, e.g., as collimated output 50 of FIG. 6A. By contrast, the same is not necessarily true for "dark" crude oil samples. Though black to the eye, the inventors have recognized that the issue is not one of color but of scattering by particulates. Specifically, when a collimated beam of light encounters microscopic asphaltene particles, NIR-wavelength rays tend to be deflected off-axis, as shown at 52 of FIG. 6B. Thus, even if those wavelengths were not actually absorbed by compounds in the sample, the scattered rays fail to reach the spectrometer's detector, making the sample appear spectroscopically "dark." The usual consequence of scattering is severe distortion of the spectral baseline.

Figure 11A:
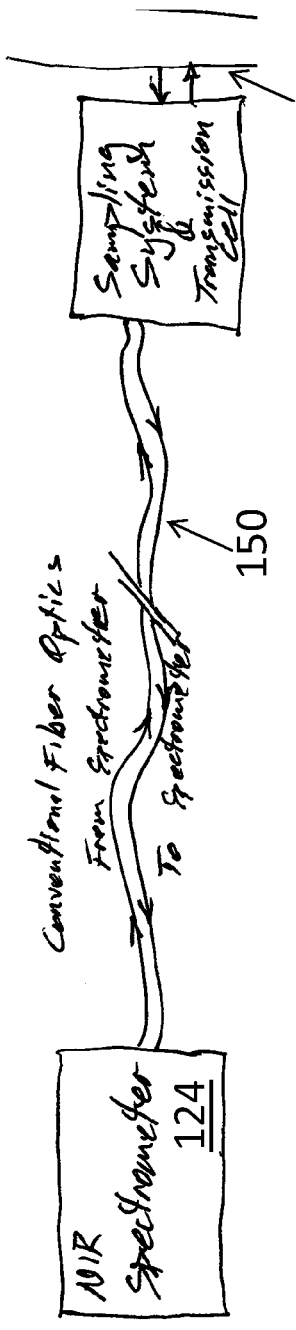
FIGS. 11A-11C are diagrammatic views of alternate configurations of the embodiment of FIG. 8.
Figure 11B:
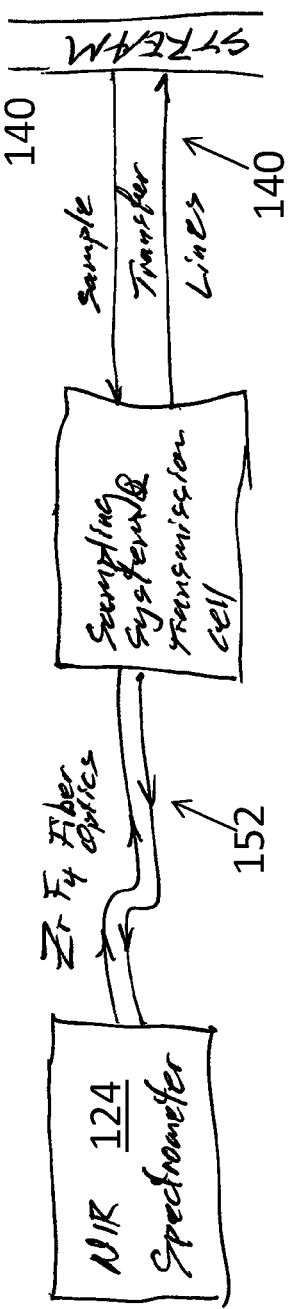
Figure 11C:
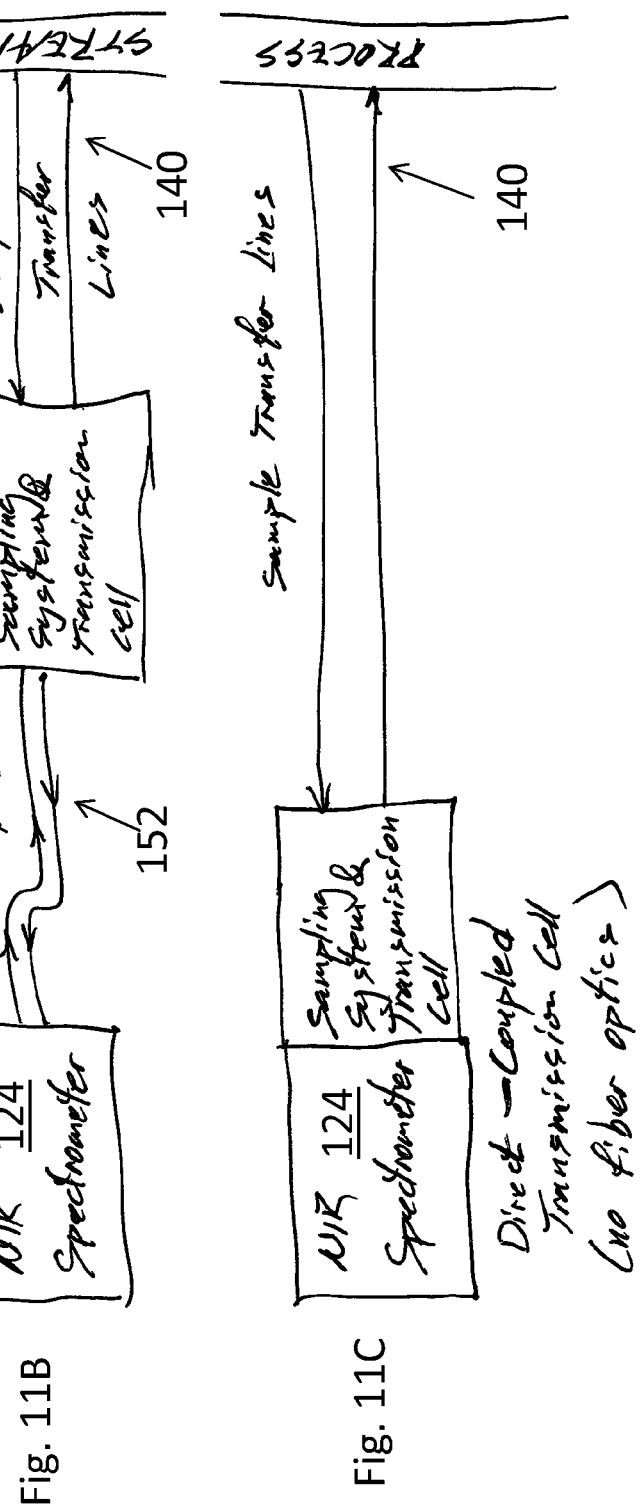

The present inventors have recognized that such scattering effects may be minimized or eliminated by using NIR overtones at longer wavelengths, specifically at the first combination overtone (FCO) occurring at 2000-2500 nm (see, e.g., FIG. 7). This, however, is above the optical cutoff for conventional NIR fibers. One approach for addressing this problem and gaining access to the FCO is to instead use fiber optics made from zirconium fluoride, which are optically transparent in that wavelength range, such as shown at 152 of FIG. 11B. But zirconium fluoride fibers also are more expensive and fragile compared with conventional fibers, which as a practical matter also reduces how far the optical cell and sampling system can be installed from the spectrometer. Alternatively, fiber optics can be eliminated altogether in favor of a direct optical coupling between spectrometer and transmission cell, such as shown in FIG. 11C. Both approaches permit measurement of a sample's spectral response in the FCO and may thereby mitigate problems associated with scattering. However, the higher intensity of those responses generally demands a corresponding reduction of pathlength to a value in the range of 0.3-0.5 mm to maintain peak absorbance values below levels where photometric nonlinearity and noise adversely impact spectral quality. While these approaches address the scattering problem, the optical pathlength of the measurement cell is now so small that even at 80° C., relatively high pressures would be required to achieve flow rates of 20-60 mL/minute for heavy crude oils with API gravity values below about 15 degrees. So while these approaches may be usable for some applications, the relatively high pressures may render them impractical for use in many instances.

An apparent dilemma therefore attaches to the analysis of heavy, scattering materials encountered in petrochemical operations. At wavelengths shorter than 2000 nm, pathlengths permit sample to flow readily but scattering effects are pronounced. But at longer wavelengths where scattering effects tend to be inconsequential, the avoidance of off-scale absorbance by the sample requires cell pathlengths that are too short to practically accommodate the representative sampling of continuously flowing high-viscosity materials.

Figure 9:
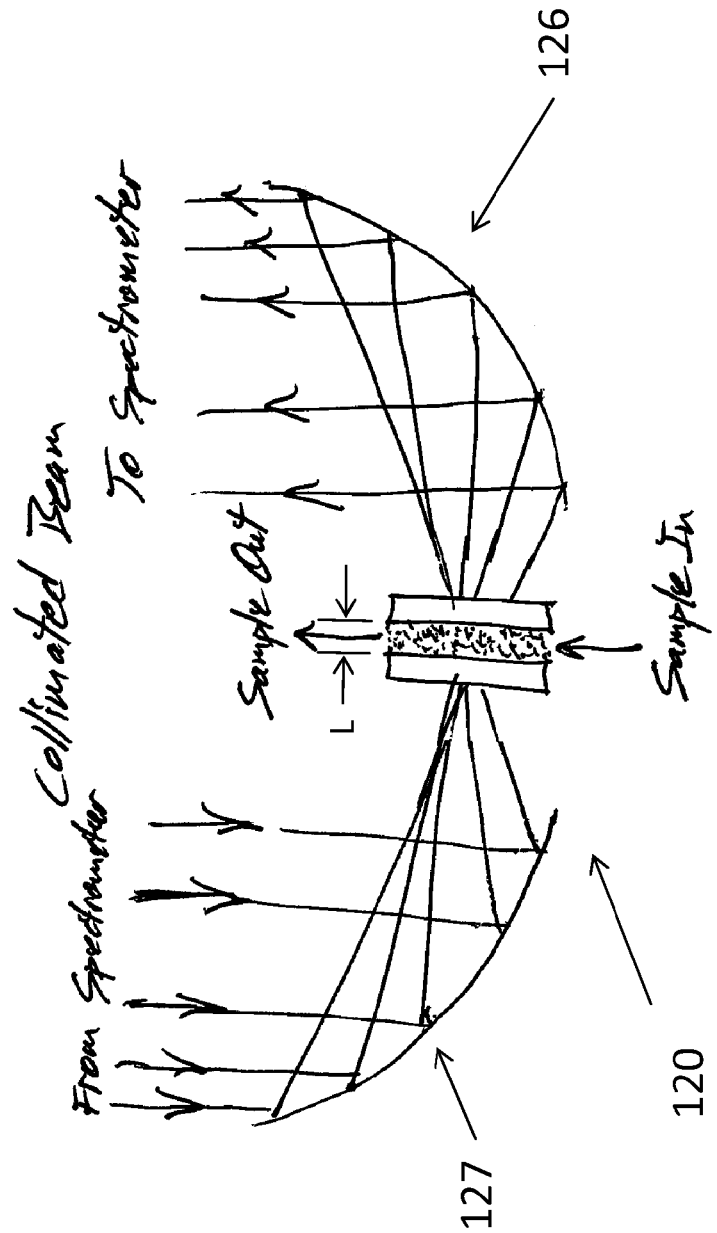
FIGS. 9 and 10 are schematic views, on an enlarged scale, of alternate aspects usable with the embodiment of FIG. 8.
Figure 10:
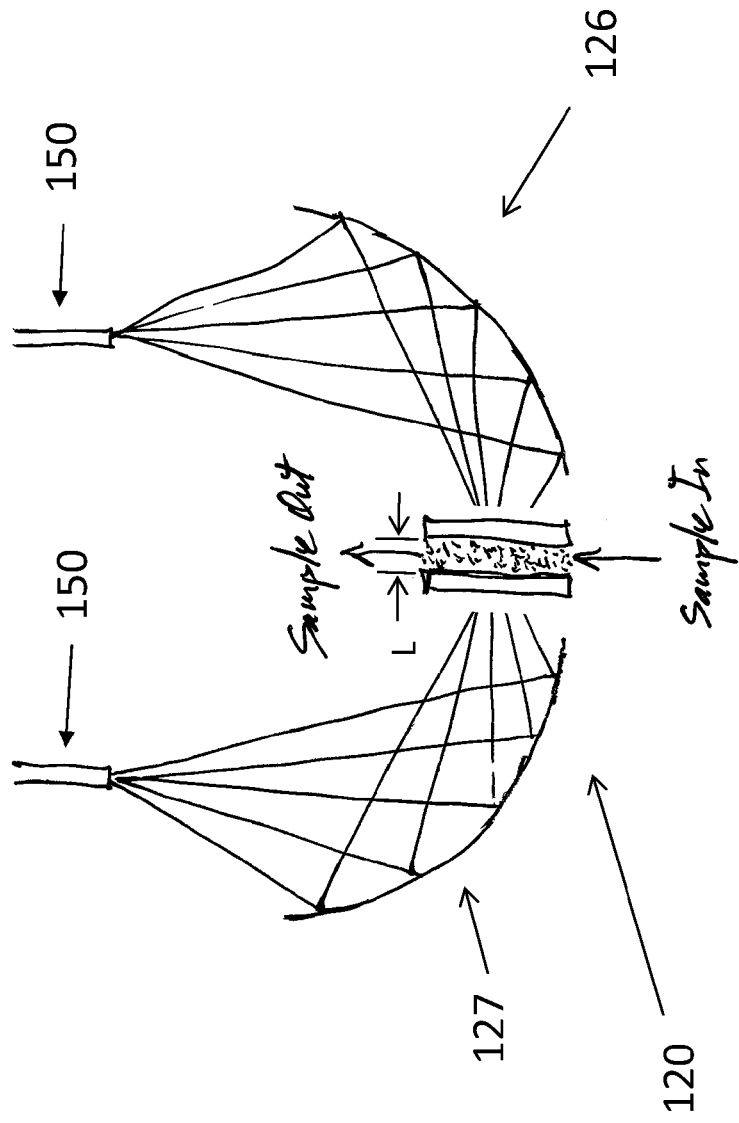

The present inventors addressed this dilemma by abandoning the optical paradigm that developed around clear, non-scattering hydrocarbon samples in favor of high-efficiency optics designed to collect light scattered by the sample. Turning now to FIGS. 9 and 10, instead of a collimated beam, embodiments of the present invention equip the transmission cell with optics 126 (e.g., having a short focal length) that effectively collect/aggregate non-collimated light emerging from the sample. As also shown, similar optics 127 may be provided to cause light transmitted by the spectrometer 124 to impinge the sample as converging rays. Rays that are not scattered by the sample simply continue to the collection optic. Those that do encounter particles are scattered across a relatively large solid angle, and a significant portion of them reach the collection optics 126. This approach enables the transmission cell 120 to be optically coupled to the spectrometer via conventional NIR grade fiber optics 150, such as shown in FIGS. 10 and 11A, e.g., to receive (and optionally send) non-collimated radiation without the need for the more fragile and expensive zirconium fluoride fibers 152 of FIG. 11B. This approach may also be used with the direct-coupled/optical conduit, such as shown in FIGS. 9 and 11C, e.g., to send and receive an otherwise conventional collimated beam to and from the optics.

NIR Spectroscopy

As discussed hereinabove, NIR analysis of crude oil is impractical at wavelengths longer than 2000 nm because a 0.5 mm pathlength optical flow cell is too small to practically permit flow at suitable rates. However, for pathlengths of 1-2 mm that do permit suitable flow rates, absorbance values in that same region would also increase 2-4 times, increasing noise and photometric nonlinearities. Embodiments of the present invention address this by measuring lower intensity overtones, e.g. the FCO, at wavelengths shorter than 2000 nm. Though optical scattering by microscopic asphaltene particles in crude oil usually results in severe distortion of the baseline in such absorbance spectra, the high-efficiency optics described herein effectively mitigate this effect while increasing signal-to-noise.

Moreover, these embodiments enable the use of conventional NIR grade fiber optics 150 to connect a NIR spectrometer with one or several remote, temperature controlled sampling cells installed near process sample taps, such as shown and discussed hereinabove in FIG. 11A.

CONCLUSION

Embodiments successfully integrate sample handling and spectroscopy into an analyzer system suited for measuring properties of crude and heavy oils.

Preservation of Sample Integrity. In contrast to crude oil, the analysis of light hydrocarbons by NIR spectrometry in the laboratory is very straightforward. A transfer syringe may be used to manually fill samples of gasoline or diesel into a conventional laboratory transmission cell, which is then placed into a holder in the spectrometer. Alternatively, a simple sampling apparatus employing a small laboratory-grade pump can be used to transfer the sample from a bottle to the cell. In neither case is any attempt made to control the temperature. Rather, spectra are measured at or around 25° C., the ambient temperature in refinery laboratories. Sampled in that manner at those temperatures, the loss of volatile compounds is negligible, which ensures that property models developed with spectra measured in the laboratory will also provide reliable results when installed on a process analyzer that preconditions the sample to 25° C.

The contrasting difficulty associated with the sampling and analysis of crude oil and heavy oils have been detailed hereinabove. In addition to the various aspects described, embodiments also advantageously provide a closed system. As described above, motor fuels generally can be analyzed conveniently at ambient temperature and pressure without compromising sample integrity through the loss of light components. But the analysis of crude oil at temperatures in the vicinity of 80° C. may result in the loss of analytically significant quantities of lower molecular weight components, were the entire sample not contained in a closed system under elevated pressure. (Hydrocarbon molecules containing six or fewer carbon atoms generally have boiling points below 80° C. while the vapor pressure at that temperature of compounds containing seven or eight carbon atoms is relatively high.)

Representative Sampling. Online or in the laboratory, the NIR analysis of motor fuels is generally done on a stationary sample. While this approach may be acceptable for homogenous motor fuels, the instant embodiments facilitate representative sampling of relatively inhomogeneous crude and heavy oils by use of flowing samples, with frequent data captures (e.g., at one per ml of sample).

Alternate Embodiments

In addition to the embodiments shown and described hereinabove, various other modifications may be made without departing from the scope of the present invention. For example, various embodiments may employ a reduced sample size volume. For example, alternative embodiments may include a reduced-volume approach in which the sample cylinder volume is 100-200 mL, sample flow rates are 5-20 mL/min, tubing sizes are reduced to less than ¼", and sample conditioning employing a single-stage fast-response heater or a suitable length of tubing in a circulating-air oven with precise temperature control. Two cylinders and displacement mixing, such as set forth in the aforementioned '461 patent may also be used.

Optional Use of Measurement Cell with Other Sensor Technology. Although embodiments shown and described herein are directed towards the use of an NIR spectrometer, it should be recognized that any number of sensor/measurement devices may be used without departing from the scope of the present invention. Examples include: a mid-IR transmission cell, e.g., with a pathlength ≤0.5 mm, in conjunction with the reduced size/volume system; an NMR (nuclear magnetic resonance) probe; and/or an acoustic flow cell for an ultrasonic spectrometer.

Figure 14:
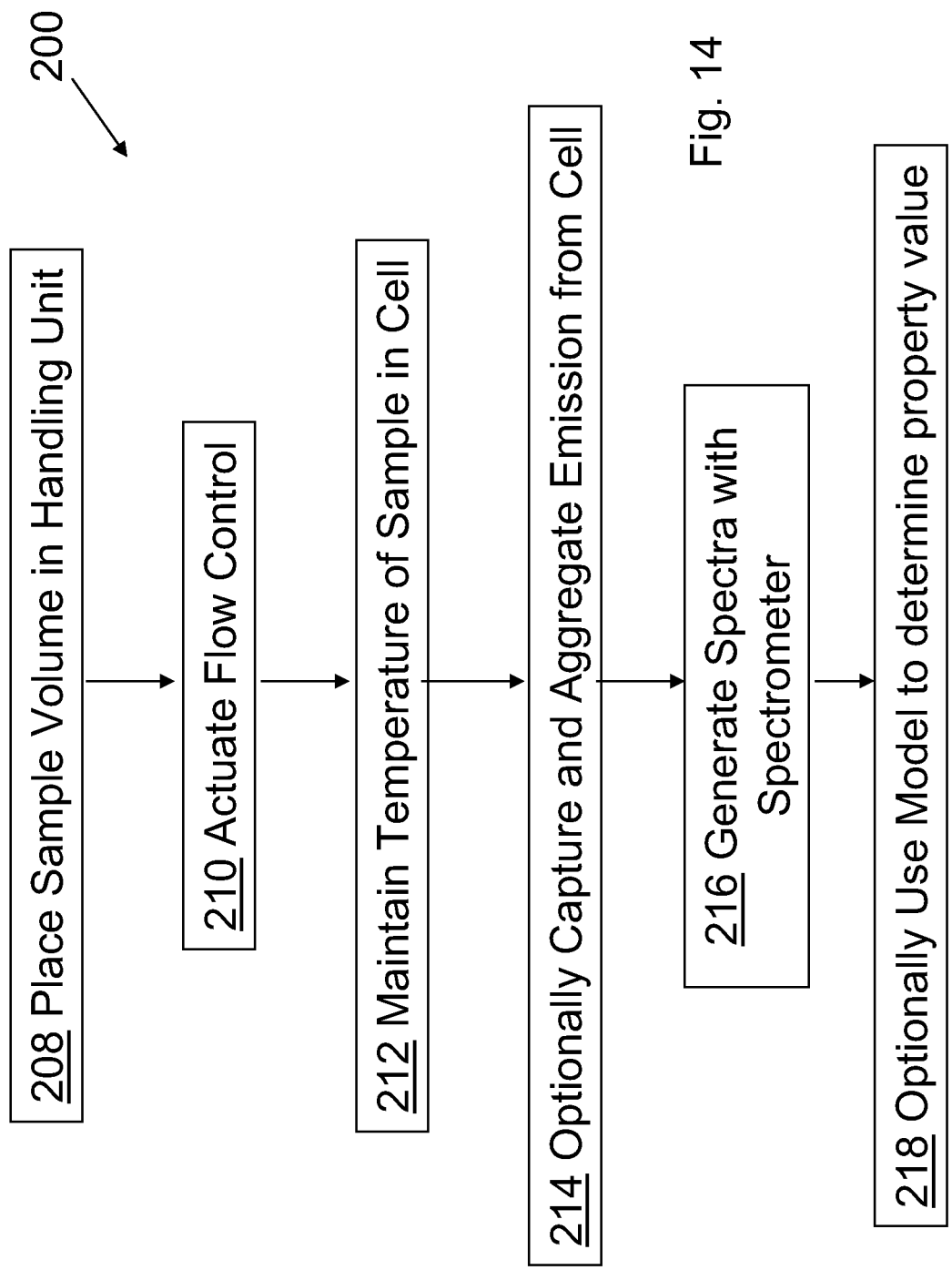
FIG. 14 is a flow chart of a representative method of the present invention.

Moreover, having described various embodiments of the apparatus of the present invention, a representative method of spectroscopic sample analysis using these embodiments will now be described with reference to FIG. 14. As shown, method 200 includes disposing 208 a sample volume within the sample handling unit of the apparatus of FIG. 8, and actuating 210 the flow control module, e.g., to maintain a substantially constant flow rate of the sample volume through the fluid flow path. With the temperature control module, the sample volume is maintained 212 at the predetermined temperature as it passes through the sample (e.g., optical transmission) cell. Optionally, with the collection optics, non-collimated radiation emerging from the optical path of the transmission cell is captured and aggregated at 214. With the spectrometer, sample spectra are measured 216 as the sample volume flows through the sample cell. Optionally, captured spectra data is used 218 in combination with one or more models suitable for determining values for properties or components of hydrocarbon mixtures, including the crude or heavy oils having asphaltenic or carbonaceous particulates, while the sample volume flows continuously through the fluid flow path.

Although various embodiments of the present invention are shown and described as being implemented off-line, it should be understood that various aspects of the invention may be implemented online, such as by directly coupling the transmission cell to a continuous fluid flow process, without departing from the scope of the present invention.

It should be noted that the various modules and other components of the embodiments discussed hereinabove may be configured as hardware, as computer readable code stored in any suitable non-transitory computer usable medium, such as ROM, RAM, flash memory, phase-change memory, magnetic disks, etc., and/or as combinations thereof, without departing from the scope of the present invention.

It should be further understood that any of the features described with respect to one of the embodiments described herein may be similarly applied to any of the other embodiments described herein without departing from the scope of the present invention.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

Having thus described the invention, what is claimed is:

1. An apparatus for off-line measurement of a property or a plurality of properties for a relatively high viscosity, inhomogeneous liquid hydrocarbon mixture including crude or heavy oils having asphaltenic or carbonaceous particulates therein, said apparatus comprising:
a fluid flow path configured to convey a predetermined sample volume of the liquid hydrocarbon mixture continuously in a downstream direction therethrough;
a sampling unit configured to receive the sample volume therein, and to continuously deliver the sample volume to the fluid flow path, the sampling unit including:
a temperature control module configured to maintain at least a portion of the sample volume at a predetermined setpoint temperature;
a homogenization module configured to distribute the particulates within the sample volume; and
a flow control module configured to maintain a substantially constant flow rate of the sample volume as it flows through the fluid flow path;
a sample cell disposed within the fluid flow path;
a spectrometer communicably coupled to the sample cell, to transmit and receive radiation to and from the sample cell;
the spectrometer configured to measure spectra for the sample volume in the sample cell, including the crude or heavy oils having asphaltenic or carbonaceous particulates; and
a processor configured to capture the spectra.

2. The apparatus of claim 1, wherein the sample cell comprises a transmission cell having an optical path with a predetermined pathlength extending therethrough.

3. The apparatus of claim 2, wherein the transmission cell includes collection optics configured to capture and aggregate non-collimated radiation emerging from the optical path, for transmission to the spectrometer.

4. The apparatus of claim 1, wherein the spectrometer is configured to measure the spectra at a predetermined rate of flow of the sample volume through the transmission cell.

5. The apparatus of claim 1, further comprising:
a model or models of spectra for the liquid hydrocarbon mixture having various properties including various concentrations of components, at the predetermined setpoint temperature; and
wherein the processor is configured to use the captured spectra in combination with said model to determine a value for the property or plurality of properties of sample volume.

6. The apparatus of claim 5, wherein the processor is configured to use the captured spectra in combination with said model or models to determine a value for the property or plurality of properties of sample volume, while the sample volume flows continuously through the fluid flow path.

7. The apparatus of claim 1, wherein the measured property is a spectrum, a multivariable array, a vector, a matrix, an equation, or combinations thereof.

8. The apparatus of claim 5, wherein the model or models are configured to produce values for properties or components when applied to the captured spectra.

9. The apparatus of claim 1, being configured for determination of properties including components of the liquid hydrocarbon mixtures in the form of crude oil used as feed in petroleum refining.

10. The apparatus of claim 9, being configured for determination of properties including components of liquid hydrocarbon mixtures having an API (American Petroleum Institute) gravity below about 22.3 degrees.

11. The apparatus of claim 9, being configured for determination of properties including components of liquid hydrocarbon mixtures having an API (American Petroleum Institute) gravity below about 15 degrees.

12. The apparatus of claim 1, wherein the spectrometer is configured to generate spectra of the sample volume at a rate of at least once per milliliter of flow through the sample cell.

13. The apparatus of claim 1, wherein the sampling unit is configured to receive a sample volume within a range of about 20 to 2200 milliliters.

14. The apparatus of claim 13, wherein the sampling unit is configured to receive a sample volume within a range of about 500 mL to 1000 mL.

15. The apparatus of claim 1, wherein the spectrometer communicably coupled to the transmission cell via NIR grade fiber optics, to transmit and receive radiation to and from the transmission cell.

16. The apparatus of claim 1, wherein a property measured is a mathematical function obtained with a spectrometer comprising at least one of an NIR spectrometer, an IR spectrometer, an NMR spectrometer, an ultrasonic spectrometer, and a microwave spectrometer.

17. The apparatus of claim 16, wherein the mathematical function is a spectrum or a multivariable array, matrix, or equation.

18. The apparatus of claim 16, wherein the temperature control module is configured to maintain the portion of the sample volume within about ±5 degrees C. of the predetermined setpoint temperature.

19. The apparatus of claim 18, wherein the temperature control module is configured to maintain the portion of the sample volume within about ±1 degree C. of the predetermined setpoint temperature.

20. The apparatus of claim 19, wherein the temperature control module is configured to maintain the portion of the sample volume disposed within the transmission cell, within about ±1 degree C. of the predetermined setpoint temperature.

21. The apparatus of claim 19, wherein the optical pathlength is within a range of about 1-2 mm.

22. The apparatus of claim 1, comprising one or more temperature detectors configured to generate temperature data for the sample volume as it flows through the sample cell.

23. The apparatus of claim 22, wherein the model or models is developed from spectra of liquid hydrocarbon mixtures having various properties or components therein, at a plurality of temperatures, and the processor is configured to capture data generated by the spectrometer and the one or more temperature detectors, and to use the data in combination with said model to determine a temperature compensated values of said properties or components in said sample volume.

24. The apparatus of claim 1, wherein the sampling unit is configured for being communicably coupled to a process through which the liquid hydrocarbon mixture flows.

25. The apparatus of claim 1, wherein the temperature control module comprises:
an actively controlled heat exchanger configured for being disposed in upstream serial fluid communication with the spectrometer;
a controller communicably coupled to said heat exchanger; and
said heat exchanger disposed in serial fluid communication downstream of said homogenization module.

26. The apparatus of claim 25, wherein the actively controlled heat exchanger comprises at least one fast-response tube.

27. The apparatus of claim 25, wherein said homogenization module comprises:
one or more sample reservoir configured to store the sample volume therein;
a sample port coupled to said reservoir;
said sample reservoir having a sample transfer pathway coupled to said sample port and extending into said reservoir;
said pathway having a plurality of orifices disposed at spaced locations along a length thereof;
one or more valves configured to selectively couple said sample port to said heat exchanger;
wherein said controller is configured to selectively actuate said one or more valves to enable a sample to flow through the sample pathway to the heat exchanger, and to actuate the heat exchanger to maintain said sample at a predetermined temperature.

28. The apparatus of claim 27, comprising a pump disposed in serial fluid communication with said heat exchanger.

29. The apparatus of claim 28, wherein said controller is configured to selectively actuate individual ones of said valves to fill said sample reservoir through said sample port.

30. The apparatus of claim 29, comprising a gas port coupled to said sample reservoir, the gas port configured for selectively receiving gas therein, to occupy volume within the sample reservoirs vacated by sample exiting through said sample port.

31. The apparatus of claim 30, wherein said reservoir comprises an other sample transfer pathway extending from a proximal end coupled to said sample port, to a distal end disposed within said reservoir, said distal end having a central axis extending obliquely relative to a longitudinal axis of said reservoir.

32. The apparatus of claim 31, wherein said other sample transfer pathway has a plurality of orifices disposed at spaced locations along a length thereof.

33. The apparatus of claim 31, wherein said reservoir comprises first and second chambers coupled to one another, said sample transfer pathway being disposed in said first chamber, and the other sample transfer pathway being disposed in said second chamber.

34. The apparatus of claim 25, wherein the actively controlled heat exchanger is an indirect contact heat exchanger.

35. The apparatus of claim 34, wherein the indirect contact heat exchanger has a thermal mass less than that of the sample fluid in a sample path thereof.

36. The apparatus of claim 34, wherein the indirect contact heat exchanger is selected from the group consisting of coil and cable heaters, flexible heaters, radiant heaters, induction heaters, microwave heaters, tubular heat exchangers, shell and tube heat exchangers, spiral tube heat exchangers, plate and frame heat exchangers, and combinations thereof.

37. A method of spectroscopic sample analysis, the method comprising:
(a) disposing a sample volume within the sample handling unit of the apparatus of claim 1;
(b) actuating the flow control module to maintain a substantially constant flow rate of the sample volume through the fluid flow path;
(c) with the temperature control module, maintaining the sample volume at the predetermined temperature as it passes through the sample cell;
(d) with the spectrometer, generating spectra for the sample volume in the sample cell; and
(e) with the processor, measuring the spectra.

38. The method of claim 37, further comprising using the processor in combination with a model or models to determine property or component values of the liquid hydrocarbon mixture, including the crude or heavy oils having asphaltenic or carbonaceous particulates, while the sample volume flows continuously through the fluid flow path.

39. The method of claim 37, further comprising using collection optics to capture and aggregate non-collimated radiation emerging from an optical path of the sample cell.

40. The method of claim 37, wherein said measuring (e) is effected at a predetermined rate of flow of the sample volume through the sample cell.

41. An apparatus for off-line measurement of a property or a plurality of properties for a relatively high viscosity, inhomogeneous liquid hydrocarbon mixture including crude or heavy oils having asphaltenic or carbonaceous particulates therein, said apparatus comprising:
- a fluid flow path configured to convey a predetermined sample volume of the liquid hydrocarbon mixture continuously in a downstream direction therethrough;
- a sampling unit configured to receive the sample volume therein, and to continuously deliver the sample volume to the fluid flow path, the sampling unit including:
  - a temperature control module configured to maintain at least a portion of the sample volume at a predetermined setpoint temperature;
  - a homogenization module configured to distribute the particulates within the sample volume; and
  - a flow control module configured to maintain a substantially constant flow rate of the sample volume as it flows through the fluid flow path;
- an optical transmission cell disposed within the fluid flow path, the transmission cell having an optical path with a predetermined pathlength extending therethrough;
- a spectrometer communicably coupled to the transmission cell, to transmit and receive radiation to and from the transmission cell;
- the transmission cell including collection optics configured to capture and aggregate non-collimated radiation emerging from the optical path, for transmission to the spectrometer;
- the spectrometer configured to generate spectra data at a predetermined rate of flow of the sample volume through the optical transmission cell;
- a model of spectra for the liquid hydrocarbon mixture having various concentrations of the components, including crude or heavy oils having asphaltenic or carbonaceous particulates therein, at the predetermined setpoint temperature; and
- a processor configured to capture and use the spectra data in combination with said model to determine a concentration of said components, including the crude or heavy oils having asphaltenic or carbonaceous particulates, while the sample volume flows continuously through the fluid flow path.

* * * * *